(12) United States Patent
McClung et al.

(10) Patent No.: US 12,714,353 B1
(45) Date of Patent: Aug. 25, 2026

(54) EMERGENCY CARDIAC AND ELECTROCARDIOGRAM ELECTRODE PLACEMENT SYSTEM WITH ARTIFICIAL INTELLIGENCE

(71) Applicant: CB Innovations, LLC, Carlsbad, CA (US)

(72) Inventors: Christian McClung, Rancho Santa Fe, CA (US); Stephen Dunphy, Carlsbad, CA (US)

(73) Assignee: CB Innovations, LLC, Carlsbad, CA (US)

( * ) Notice: Subject to any disclaimer, the term of this patent is extended or adjusted under 35 U.S.C. 154(b) by 0 days.

(21) Appl. No.: 19/080,523

(22) Filed: Mar. 14, 2025

Related U.S. Application Data

(63) Continuation of application No. 18/221,196, filed on Jul. 12, 2023, now Pat. No. 12,251,227, which is a continuation of application No. 16/428,927, filed on May 31, 2019, now Pat. No. 11,701,048, which is a continuation-in-part of application No. 15/990,651, filed on May 27, 2018, now Pat. No. 10,881,313, which is a continuation-in-part of application No. 15/853,578, filed on Dec. 22, 2017, now Pat. No. 9,986,929.

(60) Provisional application No. 62/680,552, filed on Jun. 4, 2018, provisional application No. 62/679,876, filed on Jun. 3, 2018, provisional application No. 62/679,856, filed on Jun. 3, 2018, provisional application No. 62/679,874, filed on Jun. 3, 2018, (Continued)

(51) Int. Cl.

| | |
|---|---|
| ***A61B 5/364*** | (2021.01) |
| ***A61B 5/00*** | (2006.01) |
| ***A61B 5/01*** | (2006.01) |
| ***A61B 5/08*** | (2006.01) |
| ***A61B 5/1455*** | (2006.01) |
| ***A61B 5/332*** | (2021.01) |

(52) U.S. Cl.

CPC ............ *A61B 5/332* (2021.01); *A61B 5/0006* (2013.01); *A61B 5/01* (2013.01); *A61B 5/0816* (2013.01); *A61B 5/14552* (2013.01); *A61B 5/364* (2021.01); *A61B 5/6833* (2013.01); *A61B 5/7264* (2013.01); *A61B 5/7275* (2013.01); *A61B 5/7405* (2013.01); *A61B 5/746* (2013.01)

(58) Field of Classification Search

CPC ....... A61B 5/332; A61B 5/364; A61B 5/0006; A61B 5/01; A61B 5/0816; A61B 5/14552; A61B 5/6833; A61B 5/7264; A61B 5/7275; A61B 5/7405; A61B 5/746

USPC .................................................. 600/392, 301

See application file for complete search history.

(56) References Cited

U.S. PATENT DOCUMENTS 9,101,264 B2 * 8/2015 Acquista .............. A61B 5/0004
9,247,891 B2 * 2/2016 Vos ........................ A61B 5/349

(Continued)

*Primary Examiner* — Naomi J Small

(74) *Attorney, Agent, or Firm* — Clause Eight; Michael Catania

(57) ABSTRACT

An emergency cardiac and electrocardiogram (ECG) electrode placement device with artificial intelligence is disclosed herein. The emergency cardiac and electrocardiogram (ECG) electrode placement device incorporates electrical conducting materials and elastic material into a pad that is applied to a chest wall of a patient, which places multiple electrodes in the appropriate anatomic locations on the patient to quickly obtain an ECG in a pre-hospital setting. The AI program continuously runs EKGs to continuously monitor a patient.

16 Claims, 40 Drawing Sheets

Related U.S. Application Data provisional application No. 62/679,022, filed on Jun. 1, 2018, provisional application No. 62/530,144, filed on Jul. 8, 2017, provisional application No. 62/465,752, filed on Mar. 1, 2017.

(56) References Cited

U.S. PATENT DOCUMENTS

| | | | | |
|---|---|---|---|---|
| 2002/0099277 | A1* | 7/2002 | Harry | A61B 5/0002<br>600/301 |
| 2010/0298895 | A1* | 11/2010 | Ghaffari | A61B 1/00082<br>607/116 |
| 2012/0136242 | A1* | 5/2012 | Qi | A61B 5/026<br>604/95.01 |
| 2018/0032691 | A1* | 2/2018 | Zur | A61B 5/002 |
| 2022/0160208 | A1* | 5/2022 | Liao | A61B 5/202 |

* cited by examiner

EMERGENCY CARDIAC AND ELECTROCARDIOGRAM ELECTRODE PLACEMENT SYSTEM WITH ARTIFICIAL INTELLIGENCE

CROSS REFERENCES TO RELATED APPLICATIONS

The Present Application is a continuation application of U.S. patent application Ser. No. 18/221,196, filed on Jul. 12, 2023, which is a continuation application of U.S. patent application Ser. No. 16/428,927, filed on May 31, 2019, now U.S. Pat. No. 11,701,048, issued on Jul. 18, 2023, which is a continuation-in-part application of U.S. patent application Ser. No. 15/990,651, filed on May 27, 2018, now U.S. Pat. No. 10,881,313, issued on Jan. 5, 2021, which is a continuation application of U.S. patent application Ser. No. 15/853,578, filed on Dec. 22, 2017, now U.S. Pat. No. 9,986,929, issued on Jun. 5, 2018, which claims priority to U.S. Provisional Patent Application No. 62/465,752, filed on Mar. 1, 2017, and also claims priority to 62/530,144, filed on Jul. 8, 2017, U.S. patent application Ser. No. 16/428,927 also claims priority U.S. Provisional Patent Application No. 62/679,856, filed on Jun. 3, 2018, U.S. Provisional Patent Application No. 62/679,874, filed on Jun. 3, 2018, U.S. Provisional Patent Application No. 62/679,022, filed on Jun. 1, 2018, U.S. Provisional Patent Application No. 62/679,876, filed on Jun. 3, 2018, and U.S. Provisional Patent Application No. 62/680,552, filed on Jun. 4, 2018, each of the above mentioned applications is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to ECG devices.

Description of the Related Art

The electrocardiogram (ECG) is an essential test that provides medical professionals with essential information in the management of patients with a variety of conditions. It is not only of significant importance in the evaluation and management of patients with chest pain, but also in patients with shortness of breath, syncope, dizziness, seizures, altered mental status, stroke, psychiatric conditions, overdose, palpitations and many other conditions. It is a bulky system with a multitude of wires and connections.

The ECG provides critical data to the health care provider in managing patients with multiple medical issues. The time to obtain this data is critical and often delayed by the current technology. Minutes can become critical in the patient with an acute myocardial infarction (heart attack).

Historically, there is training in the interpretation of ECG data, as well as placement of electrodes on the chest of each patient in anatomically specific positions.

Current ECG placement is done by technicians and providers of varying medical background, including paramedics, health care technicians, nursing assistants, nurses, and doctors. The current technology is bulky, with many wires and cables. The placement of the electrodes in the acquisition of an ECG is specific and requires special training. ECG acquisition is often limited and/or delayed by multiple factors such as body sweat, ability to transport the ECG device into confined areas, performance of concomitant medical procedures such as cardiopulmonary resuscitation (CPR). Because of many limitations, medical providers must make rapid decisions and potentially delay medical care while ECG testing is done. As emergency medicine providers, the inventors have identified a need for more rapid placement of the ECG electrodes, a more portable and manageable system that will not compromise medical care, and the need to eliminate electrode placement errors.

Sujdak, U.S. Pat. No. 6,847,836 for an Emergency ECG Electrode Chest Pad discloses a chest adapted for use in an emergency room.

Dominguez, U.S. Pat. No. 6,560,473 for a Disposable ECG Chest Electrode Template With Built-In Defibrillation Electrodes discloses a template that carries ten electrodes.

Most of the prior art involves developing non-conforming devices that have to be sized independently and are impractical in the confined quarters of an ambulance. Most of the prior art does not address the ability to withstand the application to a chest wall that is diaphoretic or rapidly moving. The devices are bulky and often have a large footprint thereby obviating the application of other support devices or obscuring radiologic studies. There is very little attention to the ability to reduce the frequency of lead detachment. Nor is there much attention to conforming to multiple ECG recording devices which typically occurs during periods of transfer of care from pre-hospital to emergency department to inpatient units. The need to obtain serial measurements with a high degree of reproducibility is also missed by the prior art as subtle physiologic changes can suggest significant pathology warranting immediate intervention.

Current management of patients with chest pain presenting to an emergency room is outdated. Patients that present to the emergency department for chest pain that are having a heart attack (acute myocardial infarction) are initially evaluated with an electrocardiogram or EKG also called an ECG. This EKG is then interpreted by a trained physician. Unfortunately, up to 50% of the initial EKGs can be normal despite presenting with a pending heart attack. This lack of sensitivity for the initial EKG is why it is so important to obtain multiple serial EKGs to note the subtle electrical changes that help us diagnose a heart attack. Delays in EKG acquisition, interpretation and systematic errors in EKG electrode placement all compound the problem. Initial assessment begins with a triage nurse evaluation with vital signs and an EKG is performed. Typically the EKG is rushed to a physician to interpret the EKG alone in absence of seeing the patient and this happens well over 20 times a shift. If that EKG is reassuring and there are no available beds in the ER, the patient is often kept in the waiting room while awaiting further evaluation by a provider (physician, physician assistant or nurse practitioner). Patients left in the waiting room with complaints of chest pain are a specific high risk population. Current trends in emergency department care highlight overcrowding and extending wait times. Most emergency departments are affected by high demand, and increasing volume especially in the current healthcare climate. The waiting room is a dangerous place to be.

BRIEF SUMMARY OF THE INVENTION

The present invention is a system with an emergency cardiac and electrocardiogram (ECG) electrode placement device ("EXG device") and machine running an AI program that incorporates electrical conducting materials and elastic material into a pad that is applied to the chest wall placing the electrodes in the appropriate anatomic locations on a patient. The EXG device solves the problem of lead detachment, lead reversal, inability to apply leads due to extremes in physiology, and lack of reproducibility to measure subtle changes. The ease of use with EXG device allows for acquisition of ECGs that would not have been obtained and therefore limits the opportunity loss of delays in diagnosis and treatment.

Creation of this device will reduce the time to complete an electrocardiogram (ECG) in the pre-hospital and emergency setting, eliminate systematic error in placement and interpretation of an ECG electrode, maintain and place electrodes in the proper anatomic locations across all body types, will not delay management in critical case, maintain proper skin contact through different physiologic responses such as sweat, cold and heat, as well as through medical treatment such as CPR, be easy to train providers in application and placement of ECG electrodes, and be adaptable to scenarios where space and situations limit ECG placement.

One aspect of the present invention is an emergency cardiac and electrocardiogram (ECG) electrode placement device with AI. The device comprises a body, electrodes, cables and an electrode connector. The body preferably comprises a first extension member, a second extension member, a third extension member, a fourth extension member and a fifth extensions member. The body preferably comprises a base layer composed of a flexible material, an adhesive layer composed of a flexible material, and a backing layer attached to an adhesive surface of the adhesive layer. Each of the electrodes comprises a connection stud, a contact pad interface and a contact pad. The electrode connector is positioned on the body. Each of the second extension member, the third extension member, the fourth extension member and the fifth extension member extends outward from the first extension member. Each cable of the plurality of cables is positioned between the base layer and the adhesive layer, and connected to a corresponding electrode of the plurality of electrodes and connected to the electrode connector. The first extension member comprises a first electrode, a second electrode, a third electrode, a fourth electrode, a fifth electrode and a sixth electrode of the plurality of electrodes. A seventh electrode of the plurality of electrodes is positioned at a far end of the second extension member. An eight electrode of the plurality of electrodes is positioned at a far end of the third extension member. A ninth electrode of the plurality of electrodes is positioned at a far end of the fourth extension member. A tenth electrode of the plurality of electrodes is positioned at a far end of the fifth extension member. An AI program continuously runs EKGs to continuously monitor a patient.

Another aspect of the present invention is an ergonomic cardiac and electrocardiogram (ECG) electrode system. The system comprises a device, and an EKG machine running an AI program. The device comprises a body composed of a plurality of extension members, wherein the body comprises a main layer having a top surface an adhesive surface, and a backing layer attached to an adhesive surface of the adhesive layer, an electrical conducting elastic material is incorporated into the top surface, a plurality of electrodes, each of the plurality of electrodes positioned on the adhesive surface of the main layer, and an electrode connector cable extending from the body. The AI program continuously runs EKGs to continuously monitor a patient.

Another aspect of the present invention is an emergency cardiac and electrocardiogram electrode placement device comprising a cable management module, a body, a plurality of electrodes and a plurality of cables. The cable management module comprises an upper cover, an upper guide piece, a lower guide piece and a lower cover wherein each of the upper guide piece and the lower guide piece has a plurality of channel therein. The body is composed of a first extension member, a second extension member, a third extension member, a fourth extension member and a fifth extensions member. The body comprises a base layer composed of a flexible material, an adhesive layer composed of a flexible material, and a backing layer attached to an adhesive surface of the adhesive layer. Each of the plurality of electrodes comprises a connection stud, a contact pad interface and a contact pad. Each of the second extension member, the third extension member, the fourth extension member and the fifth extension member extends outward from the cable management module. Each cable of the plurality of cables is positioned between the base layer and the adhesive layer, routed through a channel of the plurality of channels, and connected to a corresponding electrode of the plurality of electrodes and the electrode connector.

Yet another aspect of the present invention is a method for monitoring a patient having a cardiac event. The method comprises sending a signal from an ECG device on a patient via a transmitter to a machine configured to run an AI program. The method also comprises interpreting the signal at the machine suing the AI program to monitor cardiac conditions for the patient. The method also comprises comparing the cardiac conditions to previous cardiac conditions to determine a difference. The method also comprises generating a warning if a cardiac event is detected by the AI program.

Yet another aspect of the present invention is a prehospital artificial intelligence continuous EKG reading and interpretation placement system. The system comprises an emergency cardiac and electrocardiogram (ECG) electrode device with a first wireless transmitter, and a PACER system or a mobile communication device with a PACER mobile application. The ECG device with incorporated wireless transmitter and linking to the PACER system enables identification of evolving myocardial infarction and subtle changes consistent with acute coronary syndrome. The PACER system or the PACER mobile application evaluates rapid reassessments of EKG wave morphology and rhythm changes to predict and diagnose acute coronary or significant cardiac arrhythmias using tangible software configured with instructions to determine specific changes such as ST segment elevations of more than 1 mm in contiguous leads in comparison to prior EKGs or set norms and alert multiple providers of these changes, and also records these findings and transmit them to providers, and answers the question if there is a change in diagnosis and prognostication to warrant emergent treatment.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
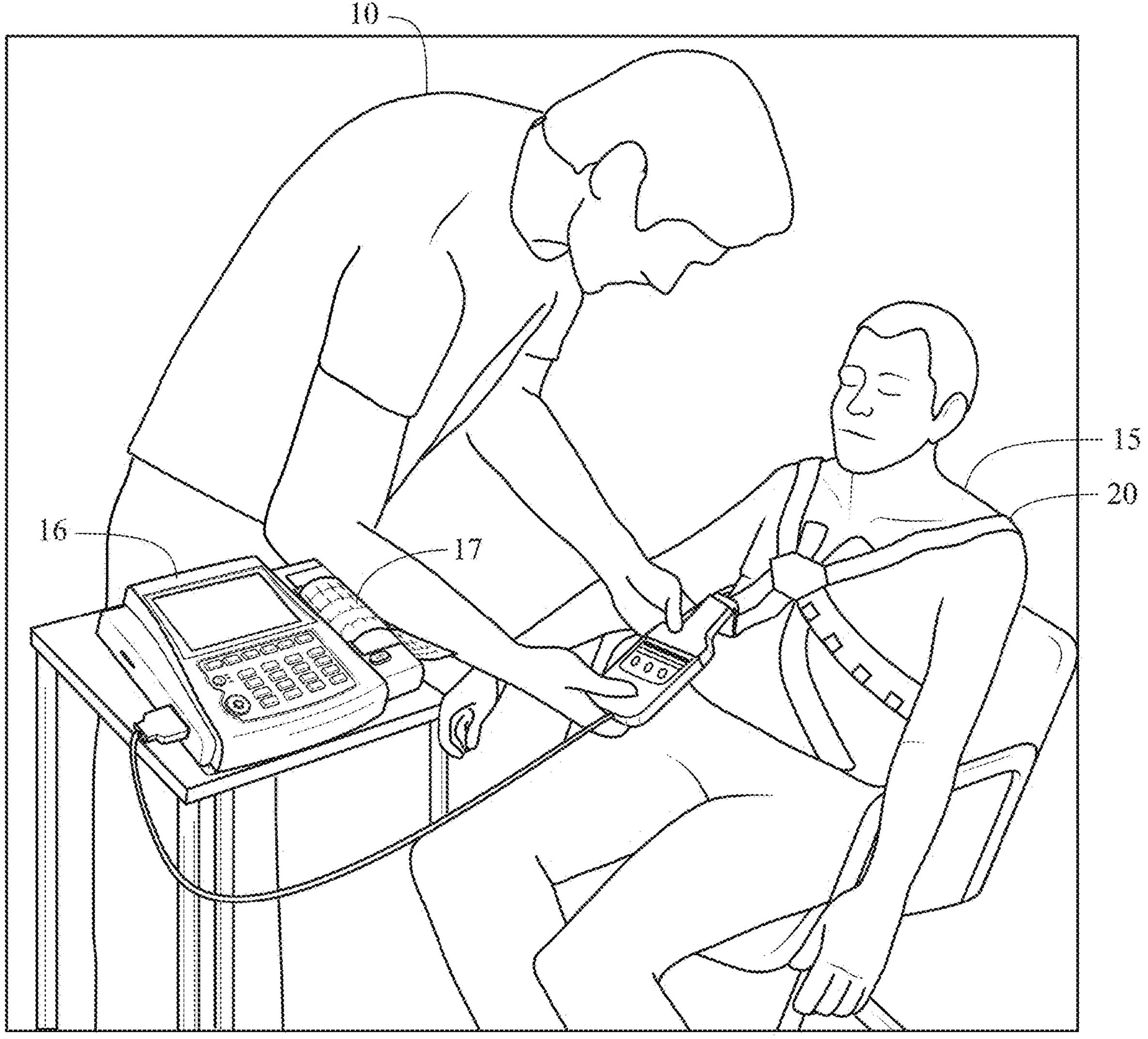
FIG. 1 is an illustration of an emergency cardiac and ECG electrode placement system used by a technician on a patient.

With current technology utilizing the EXG-system and artificial intelligence (AI) algorithms, the potential to expand the emergency department safely to include the waiting room is now feasible. The potential to monitor all patients with chest pain remotely and safely with diagnostic AI systems will decrease missed diagnosis, increase accuracy, and improve safety throughout the healthcare system. The E×G system coupled with a continuous 12 lead central monitoring system using patented artificial intelligence to detect subtle changes in the EKG regardless of patient location is now a reality. With application of a portable reliable and diagnostic EKG monitoring device, the EXG will interface wirelessly with a central processing unit capable of detecting subtle EKG changes dynamically and alert providers of these changes. It is a perfect blend of AI and healthcare aimed at saving lives. Preferably, if a cardiac event is detected, an alarm is sent to the device to signal which patient is having the cardiac event. This is important if the patient is in a waiting room at a hospital.

Current systems evaluate patients with acute coronary syndrome with point estimate EKG and serial serum enzyme testing. Recurrent episodes of chest pain and heart attack are often missed due to delays in EKG acquisition and identification for subtle changes in the EKG. These point estimates have been the only feasible option for healthcare providers, until now. Patients at high risk for disease especially in the era of emergency department overcrowding and delays and triage and patient assessment raise the risk for morbidity and mortaility. Serial assessments of ST segment and other subtle changes indicative of acute coronary syndrome are time consuming, resource consuming and not feasible with the current systems. The EXG-system, with its reliable placement, reproducible data acquisition, ease of use, mitigated motion artifact, allows diagnostic AI to monitor for subtle changes indicative of cardiac pathology continuously. The EXG-system coupled with continuous 12 lead EKG monitoring and wireless connectivity and AI processing will better identify patients with acute coronary syndrome, minimize risk of missed MI, and contribute to better patient outcomes.

The ability of AI to perform near continuous evaluation of multiple EKGs on multiple patients simultaneously is something that would be an unconventional and non-routine practice scope of any clinician. One patient could receive continuous EKGs on the order of up to 20 or more EKGs per minute. The AI engine would be able to continuously monitor multiple patients at a time with multiple EKGs done during the monitoring period, and that would not be feasible for any clinician. Imagine 20 patients undergoing 20 EKGs per minute over the course of a 20-48 hour hospital stay. Thousands of data points being continuously monitored and evaluated with diagnostic precision. This novel system approach to evaluating patients with presentations concerning for acute coronary syndrome will potentially decrease frequency of actual EKG acquisition as the AI will identify when changes occur, thus prompting repeat EKG evaluation versus predetermined arbitrary point estimate EKG acquisition. Potentially obviating need for repeat EKGs if no changes are noted. This will lead to saving lives, saving time and give clinicians increased confidence in evaluating these patients regardless of patient location.

The AI engine will receive data from a continuous signal via wireless or wired technology via the EXG device or any 12 lead continuous monitoring device attached to patient(s) to get a first EKG, second EKG and subsequent serial EKGs over set intervals that will do standard EKG interpretation but also compare second EKG and subsequent serial EKGs to the first EKG and/or baseline EKG and interpret changes. The AI engine will then be able to determine any significant changes concerning for acute coronary syndrome, arrhythmia, or other diagnostic criteria for dynamic EKG changes in the setting of acute coronary syndrome. Once changes or significant findings are made, algorithms will be in place to alert providers of these findings in real time. Data will be stored. Stored data will be available for review and integration into patient charts and records.

In summary, the EXG device will now allow diagnostic continuous 12 lead EKG monitoring easily, quickly, reliably and safely. Incorporation of the device with an AI system will decrease the risk of missed MI in the waiting room, on the patient floor, and in the emergency department. Similar benefits of an EXG-AI combination could be seen for patients who present with syncope (Sudden loss of consciousness) where the event may be related to intermittent arrhythmias that cause an unstable function of the heart and require pacemaker insertion. This EXG-AI combination essentially turns every space into a cardiac monitored space thus improving the resources for an entire hospital where patients now may wait specifically to placed on a ward with cardiac monitors as the majority of non-ICU hospital rooms do not have cardiac monitors installed.

As shown in FIG. 1, the emergency cardiac and electrocardiogram (ECG) electrode placement device ("EXG device") 20 is a worn device that incorporates electrical conducting materials and elastic material into a pad that is applied to the chest wall placing the electrodes in the appropriate anatomic locations on a patient 15. A technician 10, such as an emergency responder, places the EXG device 20 on the patient 15 and connects the EXG device 20 to an ECG machine 16 which generates an ECG 17.

Figure 3:
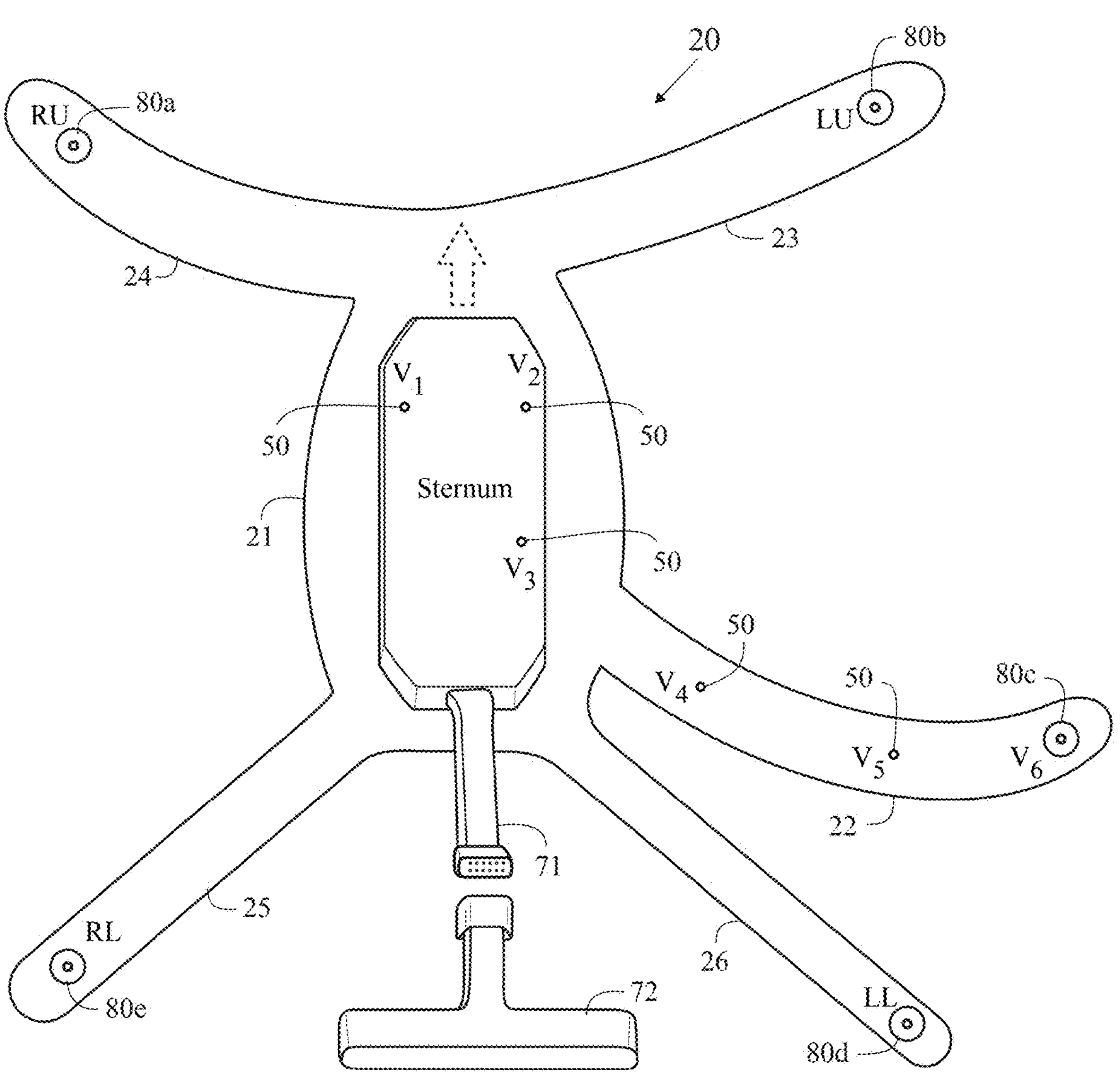
FIG. 3 is top plan view of a first embodiment of an emergency cardiac and ECG electrode placement device in an application state.

As shown in FIG. 3, the EXG device 20 preferably comprises a body 21, electrodes 50, cables 60 (not shown), and an electrode connector 71. The body 21 preferably comprises a first extension member 22, a second extension member 23, a third extension member 24, a fourth extension member 25 and a fifth extension member 26. The electrode connector 71 is positioned on the body 21. Each extension member 22-26 preferably has a width ranging from 1 cm to 10 cm, and a length ranging from 5 cm to 20 cm.

Figure 5:
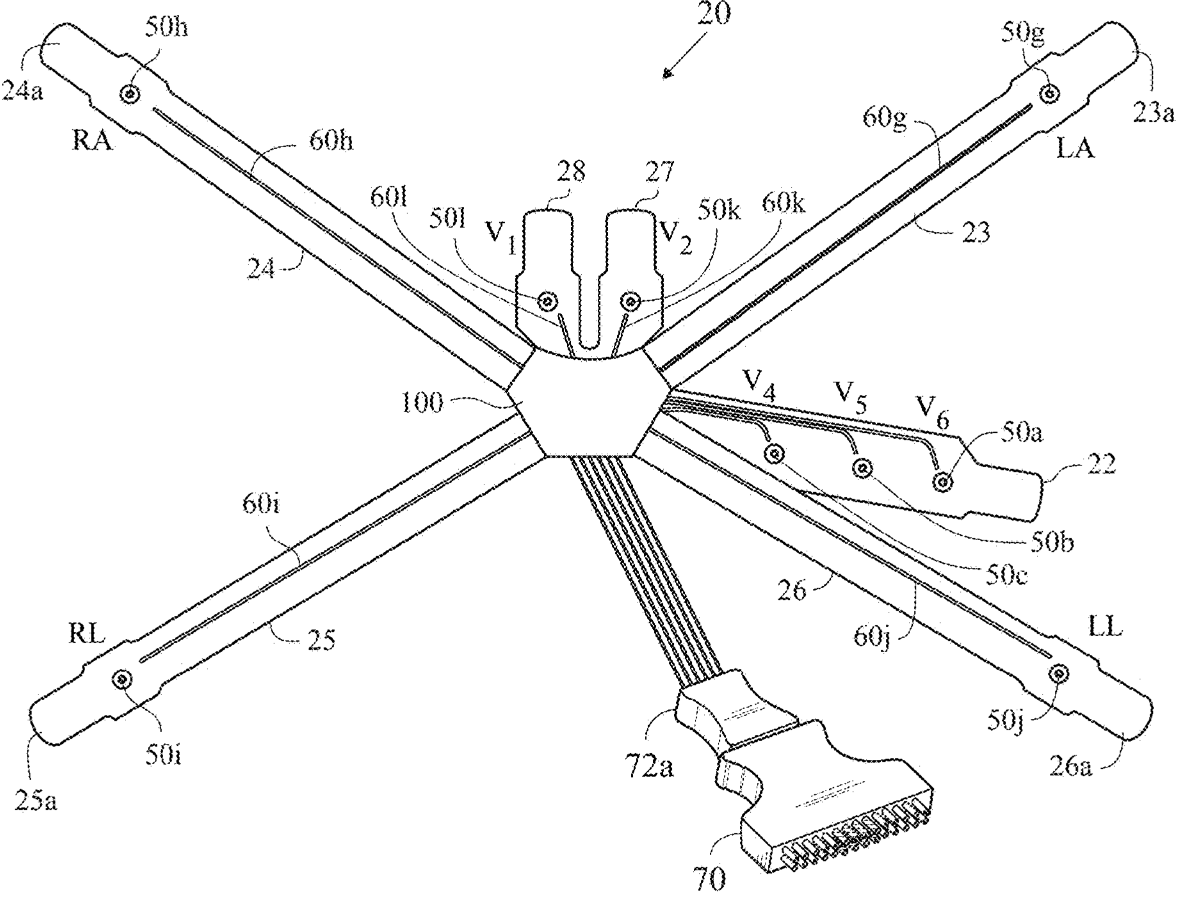
FIG. 5 is a top plan view of a second embodiment of an emergency cardiac and ECG electrode placement device in an application state.
Figure 6:
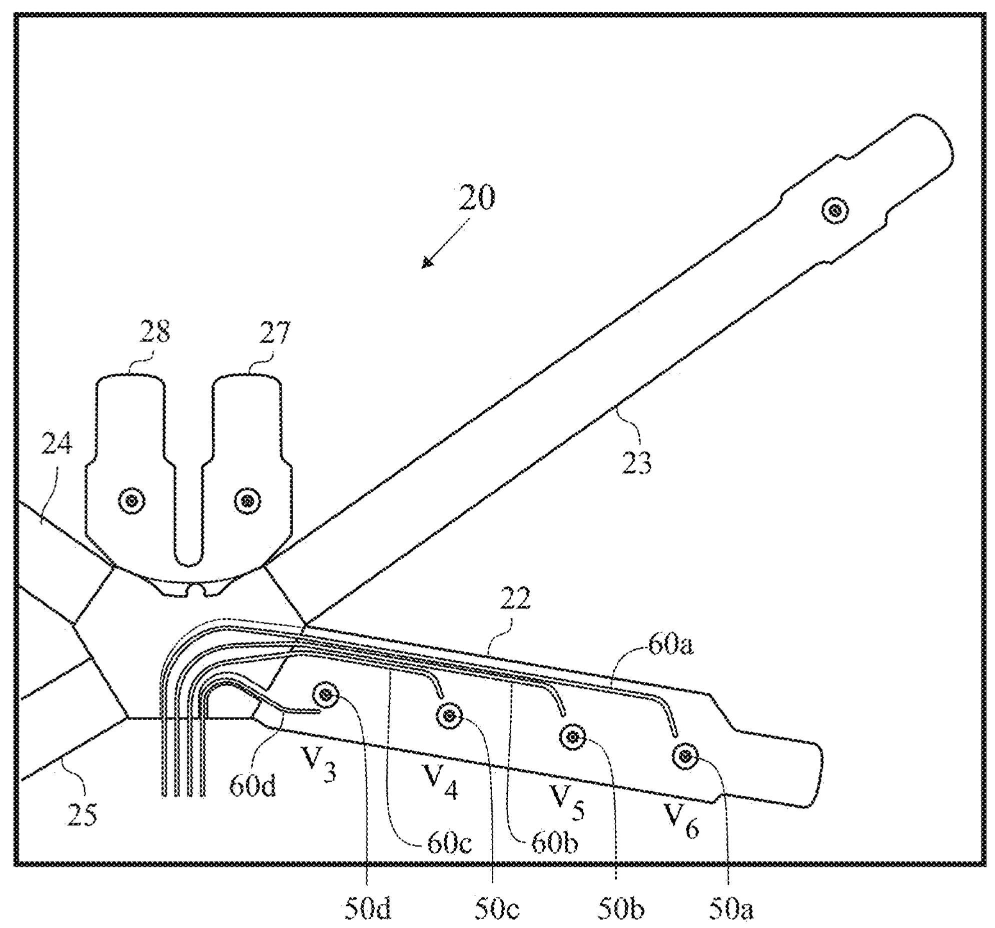
FIG. 6 is an isolated top plan view of a second embodiment of an emergency cardiac and ECG electrode placement device in an application state.
Figure 7:
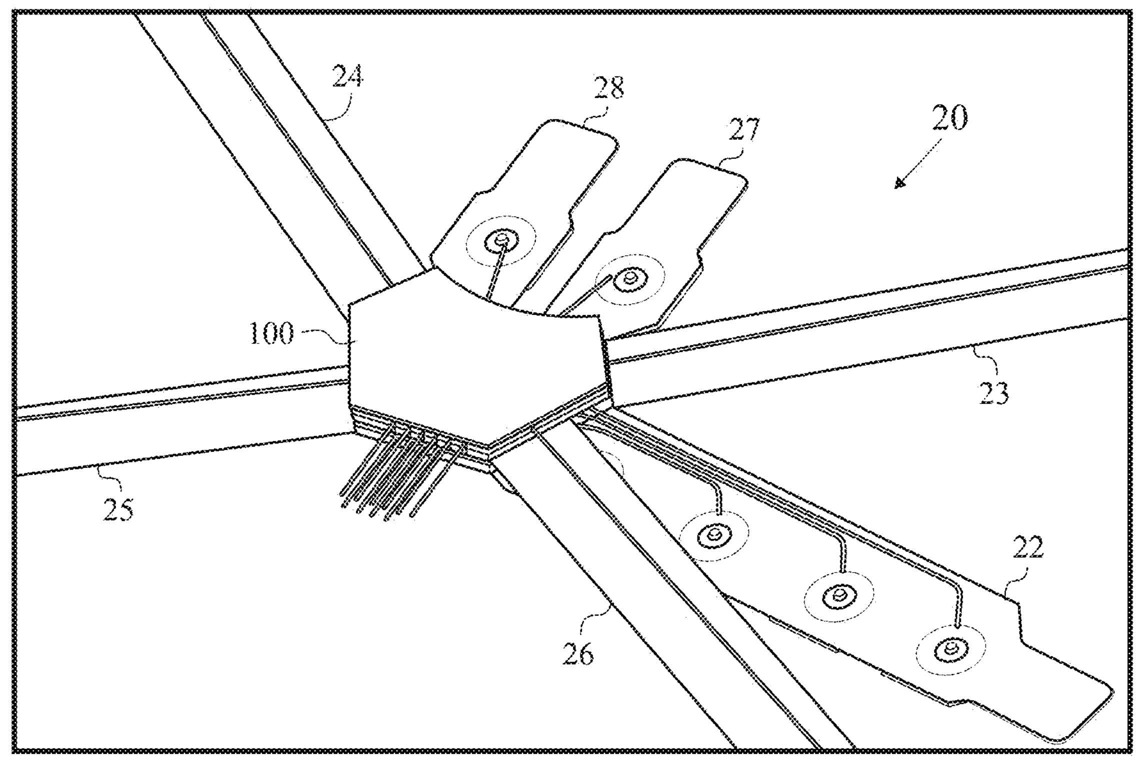
FIG. 7 is a top perspective view of a second embodiment of an emergency cardiac and ECG electrode placement device in an application state.
Figure 8:
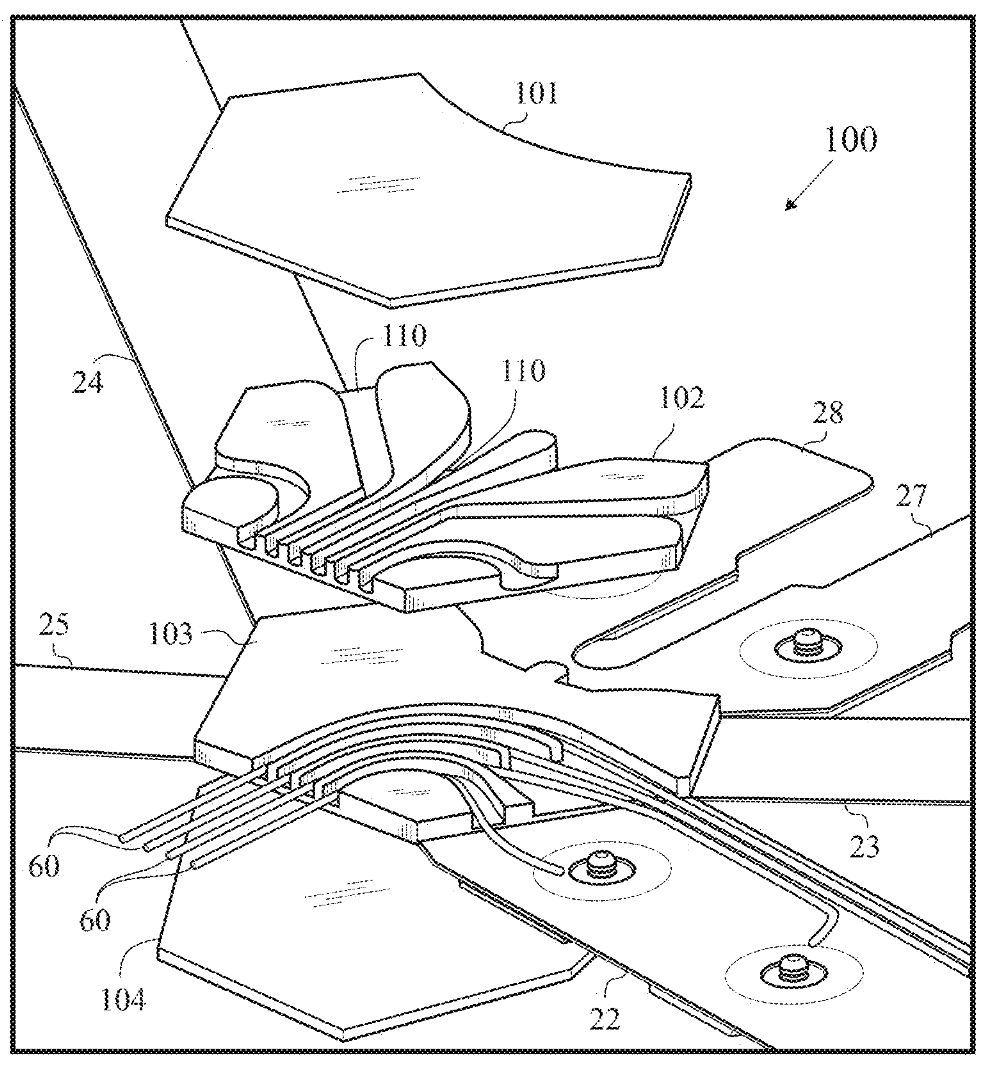
FIG. 8 is an isolated exploded view of a control module of a second embodiment of an emergency cardiac and ECG electrode placement device.

A second embodiment of EXG device 20 is shown in FIGS. 5-7. Each of the first extension member 22, the second extension member 23, the third extension member 24, the fourth extension member 25 and the fifth extension member 26 extends outward from the center of the body 21. The first extension member 22 preferably comprises a first electrode **50*a*, a second electrode 50*b*, a third electrode 50*c*, a fourth electrode 50*d*, a fifth electrode 50*e* (not shown) and a sixth electrode 50*f* (not shown). A cable 60*a* connects the electrode 50*a* to the electrode connector 71. A cable 60*b* connects the electrode 50*b* to the electrode connector 71. A cable 60c connects the electrode 50c to the electrode connector 71. A cable 60d connects the electrode 50d to the electrode connector 71. Although not shown, a cable 60e connects the electrode 50e to the electrode connector 71, and a cable 60f connects the electrode 50f to the electrode connector 71**.

A seventh electrode 50g is positioned at a far end 23a of the second extension member 23, and a cable 60g connects the electrode 50g to the electrode connector 71. An eight electrode 50h is positioned at a far end 24a of the third extension member 24, and a cable 60h connects the electrode 50h to the electrode connector 71. A ninth electrode 50i is positioned at a far end 25a of the fourth extension member 25, and a cable 60i connects the electrode 50i to the electrode connector 71. A tenth electrode 50j is positioned at a far end 26a of the fifth extension member 26, and a cable 60j connects the electrode 50j to the electrode connector 71. The far ends 23a, 24a, 25a, 26a of the extension members 23, 24, 25, 26 and even the far end of extension member 22, act as strip extensions that assist in placing the electrode correctly. This strip extension is approximately 1 to 2 inches in length as measured from the electrode.

The EXG device 20 of FIG. 5 also comprises a sixth extension member 27 with an electrode 50k and a seventh extension member 28 with an electrode 50l. A cable 60k connects the electrode 50k to the electrode connector 71, and a cable 60i connects the electrode 50l to the electrode connector 71.

The EXG device 20 of FIGS. 5-8 includes a cable management module 100. The cable management module 100 comprises an upper cover 101, an upper guide piece 102, a lower guide piece 103 and a lower cover 104. Each of the upper guide piece 102 and the lower guide piece 103 has a plurality of channels 110 therein for guiding the cables 60 therethrough. The channels 110 of the cable management module 100 allow for the extension of an extension member to fit a patient, without the cables 60 becoming tangled.

Figure 9:
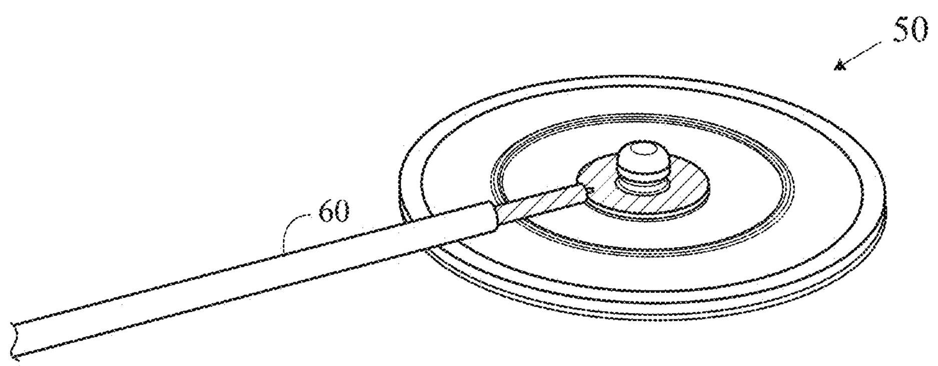
FIG. 9 is an isolated top perspective view of an electrode of an emergency cardiac and ECG electrode placement device.
Figure 10:
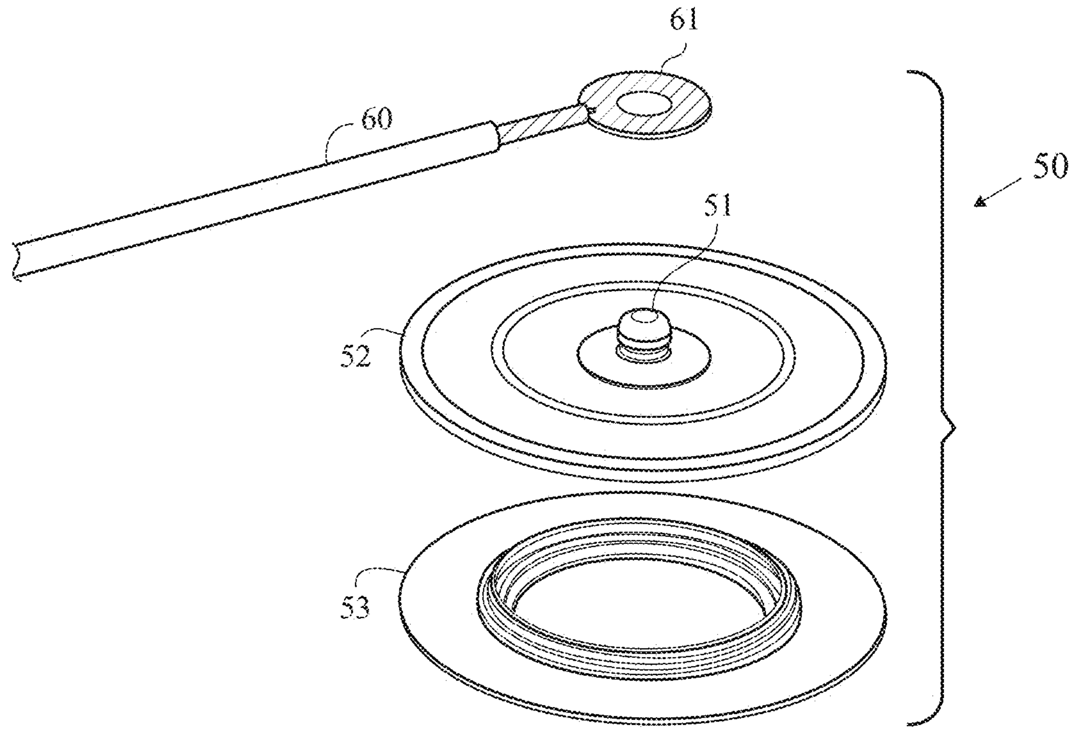
FIG. 10 is an isolated exploded view of an electrode of an emergency cardiac and ECG electrode placement device.
Figure 11:
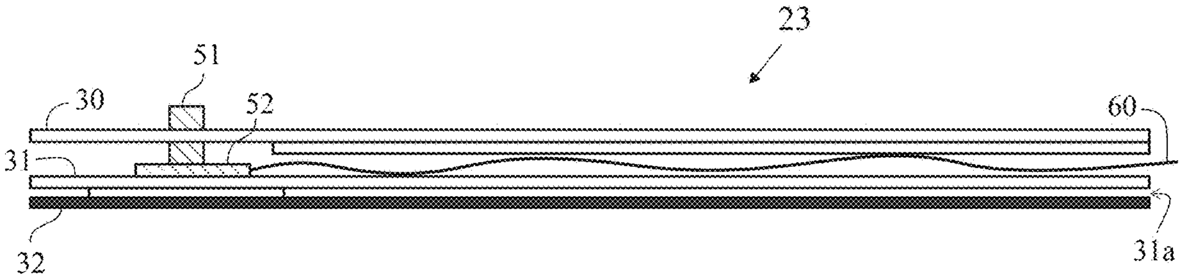
FIG. 11 is an isolated cross-sectional view of an extension of is an isolated view of an electrode of an emergency cardiac and ECG electrode placement device.

As shown in FIGS. 11, each extension member of the body 21 preferably comprises a base layer 30 composed of a flexible material, an adhesive layer 31 composed of a flexible material, and a backing layer 32 attached to an adhesive surface 31a of the adhesive layer 31. One preferred material for the flexible material is KT TAPE from Spidertech. The base layer 30 preferably has a Shore A hardness ranging from 50 to 90, which better allows for chest compressions. One preferred material for the adhesive layer is an adhesive from 3M. As shown in FIGS. 9-10, each of the electrodes 50 preferably comprises a connection stud 51, a contact pad interface 52 and a contact pad 53. Each contact pad 53 is preferably has a diameter ranging from 30 milliimters ("mm") to 40 mm, and most preferably 35 mm, to in one embedment allow for retention of a gel protector. Each contact pad 53 is preferably composed of a material from 3M. A cable connector 61 of each cable 60 is connected to a connection stud 51 of each electrode 50 preferably using a conductive epoxy. Each cable connector 61 is preferably composed of 0.2 mm thick copper, with a 26 mm inside diameter. Each cable 60 of the plurality of cables 60 is positioned between the base layer 30 and the adhesive layer 31. Each cable 60 is connected to a corresponding electrode 50 of the plurality of electrodes 50 and connected to the electrode connector 71. Each cable 60 is preferably shielded to prevent electrical interference. Each of the plurality of cables preferably as an outer diameter ranging from 0.008 inch to 0.310 inch.

Figure 2:
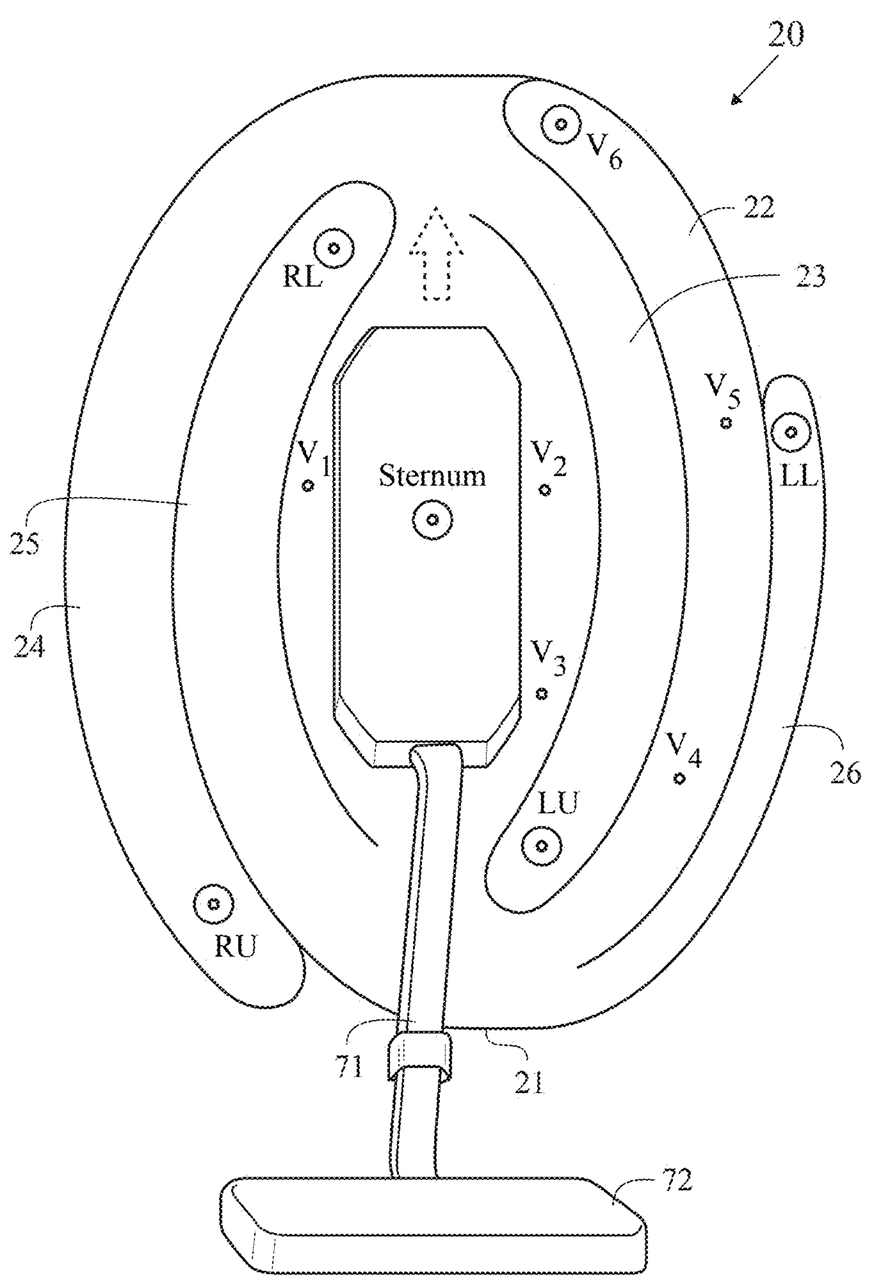
FIG. 2 is a top plan view of a first embodiment of an emergency cardiac and ECG electrode placement device in a storage state.
Figure 4:
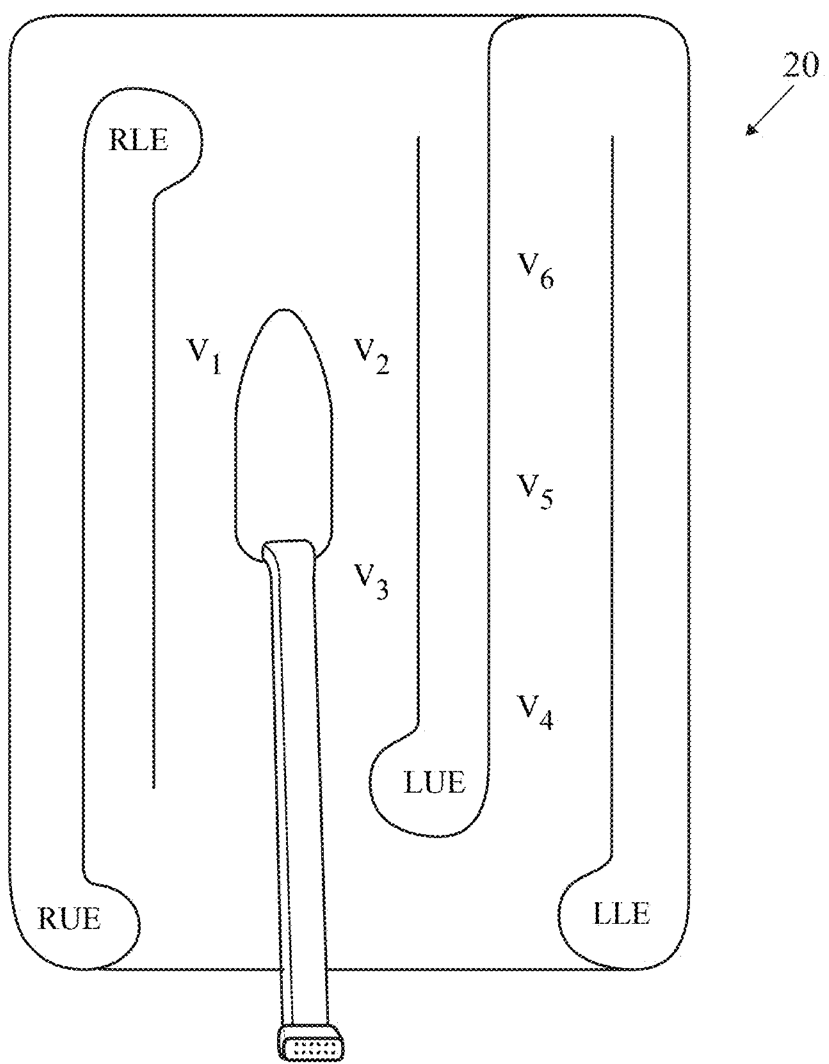
FIG. 4 is a side elevation view of a first embodiment of an emergency cardiac and ECG electrode placement device in a storage state.

As shown in FIGS. 2 and 4, the EXG device 20 is preferably provided in a compact, easily stored and transported form, that is then applied to a patient's chest wall with materials that have adhesive capabilities that preferably resist moisture and conforms to the patient's body with inherent elasticity with placement of electrodes within a pad that maintain proper anatomic ratios and locations. The EXG device 20 preferably remains adherent to the patient's body through the duration of the acute pre-hospital and transition through the emergency department and acute hospitalization care periods (which is typically three days), but the EXG device 20 remains easily removable, while tolerating physiologic changes such as sweat, fever and medical treatment such as cardiac pulmonary resuscitation ("CPR"). The EXG device 20 is clearly marked and designed to fit to the chest wall so that its application ensures proper placement of all electrodes on the patient. The incorporated electrical conducting materials come together into a single cable/wire that is either directly or indirectly joined to an ECG monitoring device. The cable has adaptor capability that allows for wireless transfer of data to an ECG monitoring device obviating the need for having a bulky ECG machine in close proximity to the patient. The single cable also eliminates the need for multiple wires on a patient. Multiple wires that could potentially interfere with diagnostic imaging such as chest radiographs, or interfere with placement of emergency medical equipment such as transcutaneous cardiac pacer pads or defibrillating pad.

The EXG device 20 reduces the time to perform ECG testing significantly. With proper training, a user can anticipate ECG acquisition in less than one minute, and potentially within seconds. Current ECG data can take several minutes or longer depending on the care setting. It is not unusual for an ECG ordered in a hospital setting to take more than 10-30 minutes.

The EXG device 20 also eliminates lead transposition error. That is, the attachment of an electrode wire in a wrong electrode.

The EXG device 20 makes ECG data more reliable and reproducible. There is no variation in lead placement while performing serial ECGs—which is often done in the hospital and pre-hospital setting. The incorporated elastic electro-conductive materials allow for this small form factor to accommodate varying body types (man, women, adult, child, obese, anorexic) while maintaining strict anatomic ratios and correct placement and ensure proper lead placement.

The ease of use of the EXG device 20 makes ECG acquisition less inconvenient and potentially improves ECG utilization in the pre-hospital setting. The EXG device 20 also reduces the frequency of lead detachment. An alternative embedment of the E×G system has wireless transfer capability that makes acquisition of the ECG in any situation feasible. The EXG device 20 preferably incorporates either integrated elastic electro-conductive materials or printable elastic electro-conductive material used in the acquisition of electrical signals from the electrodes. The EXG device 20 adheres to skin surfaces through a variety of physiologic conditions not currently met by current methods. The E×G system allows for acquisition of data in settings that standard methods currently fail. Existing technology for ECG acquisition relies on technical expertise in lead placement. Removing technical error is dependent of operator knowledge and skill, as well as interpretation of ECG data to identify systemic error in placement. The time to acquire an ECG is dependent on many factors but is limited due to the number of electrodes that are placed on the chest and torso, which then need to be attached to the ECG device. There are preferably a minimum of ten wires involved, and more electrodes are possible to allow for more specific views of the right side of the heart and/or posterior heart leads.

The EXG device 20 is preferably a single device with embedded lead placement through a wearable material (such as a fabric) with a small physical footprint with the elasticity to maintain physiologic measurement across different ages, gender and body habitus without requiring multiple sized devices.

In one embodiment, the EXG device preferably comprises: adhesive stretchable material that is breathable and water/sweat resistant; embedded elastic electroconductive material conducting electrical signals from the integrated cardiac electrodes to a central data cable; embedded elastic electroconductive material/wiring/cabling arranged to allow for stretching across body types and sizes; electrode connection port; Bluetooth capable emitter and receiver; conduction gel; and embedded electrodes (manufactured or printable).

The elastic adhesive membrane preferably provides adherence to body surface. It is preferably tolerant to moisture. The EXG device preferably incorporates electroconductive materials and electrodes that conduct signal from the skin to a single data cable/wire. The EXG device preferably expands in an elastic fashion to appropriately fit varied body types while meeting exact ratios of electrode distance without distortion. The EXG device preferably has significant stability of size and shape with elastic components to make it easily applicable to the chest wall. The EXG device preferably comes in a compact form factor.

In one embodiment, there is encapsulated expandable electroconductive material within the membrane. Within the elastic membrane is incorporated electroconductive materials that originate from each electrode to come together into a single data cable encompassing a minimum of ten ECG wires to allow for a standard twelve lead ECG (by convention there are two leads that are inferred from the ten connections).

Alternatively, the EXG device allows for the use of external electrodes. In the event that ECG monitoring equipment is not compatible with the data cable, electrodes at the ascribed anatomical locations can be accessed with standard medical cardiac monitoring and ECG devices.

In one embodiment, there is a conductive membrane at ECG electrode sites. At the ascribed electrode ECG locations is a typical electroconductive Ag/AgCL membrane to conduct current from body surface to ECG monitoring device.

In one embodiment, a data cable brings individual electrodes into one cable that encompasses a minimum of ten wires/leads of the typical ECG analysis which is then compatible with various ECG devices and wireless transfer system. Other conductive interfaces may be utilized with the invention including ones composed of graphene/carbon, nickel, and copper.

In use, one applies the EXG device 20 to an anterior chest wall overlying the sternum symmetrically at a level above the nipple line of the patient and below the sternal notch, removing the backing layer 32 to expose the adhesive surface 31*a* of the adhesive layer 31. The precordial limb is then stretched to the lateral chest wall at the mid axillary line below the nipple line. Similarly each limb will have the backing layer 32 removed in succession to expose the adhesive surface 31*a* of the adhesive layer 31. The right upper extremity limb is stretched towards the right shoulder. The left upper extremity is stretched towards the left shoulder. The right lower extremity limb is stretched to the right lower abdominal quadrant. The left lower extremity limb is stretched to the left lower abdominal quadrant. The cable is either attached to directly to the ECG device cable. Or in versions utilizing a BLUETOOTH transceiver, then the EXG device 20 is activated to sync with the BLUETOOTH transceiver that is already connected to the ECG device.

Figure 12:
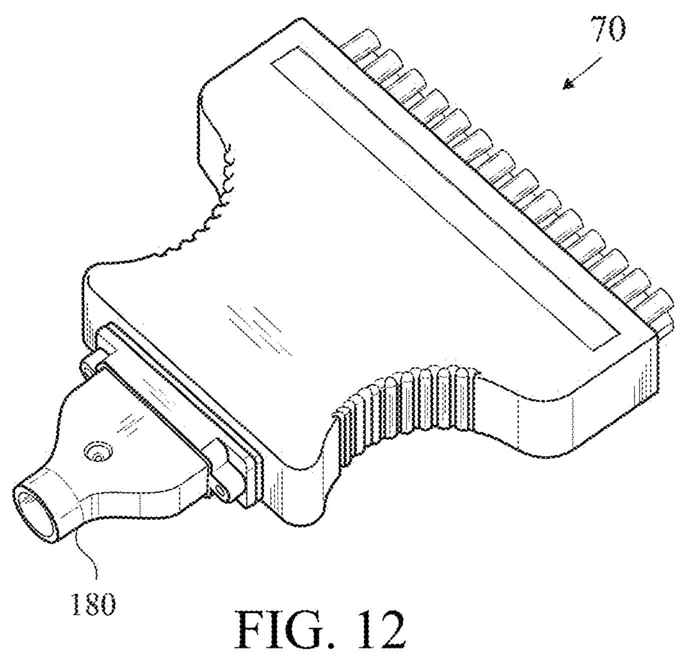
FIG. 12 is a top perspective view of a connection module for an emergency cardiac and ECG electrode placement device.
Figure 13:
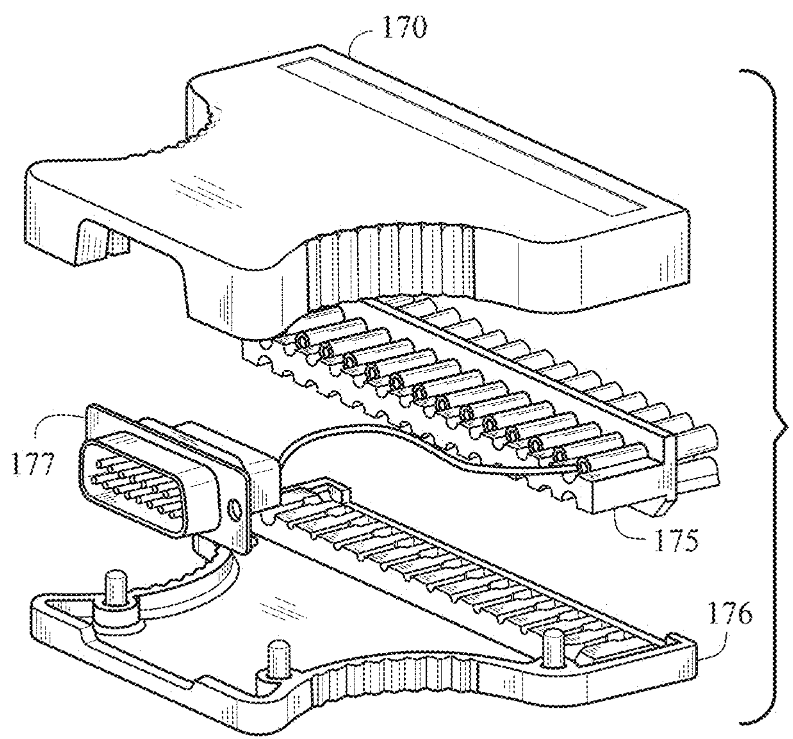
FIG. 13 is an exploded top perspective view of a connection module for an emergency cardiac and ECG electrode placement device.

A preferred embodiment of a connector module 70 is shown in FIGS. 12-13. The connector module 70 preferably comprises a top cover portion 170, a bottom cover portion 176, a plurality of connector pins 175 and a fifteen pins sub connector 177. An interface connector 180 is also shown.

Figure 14:
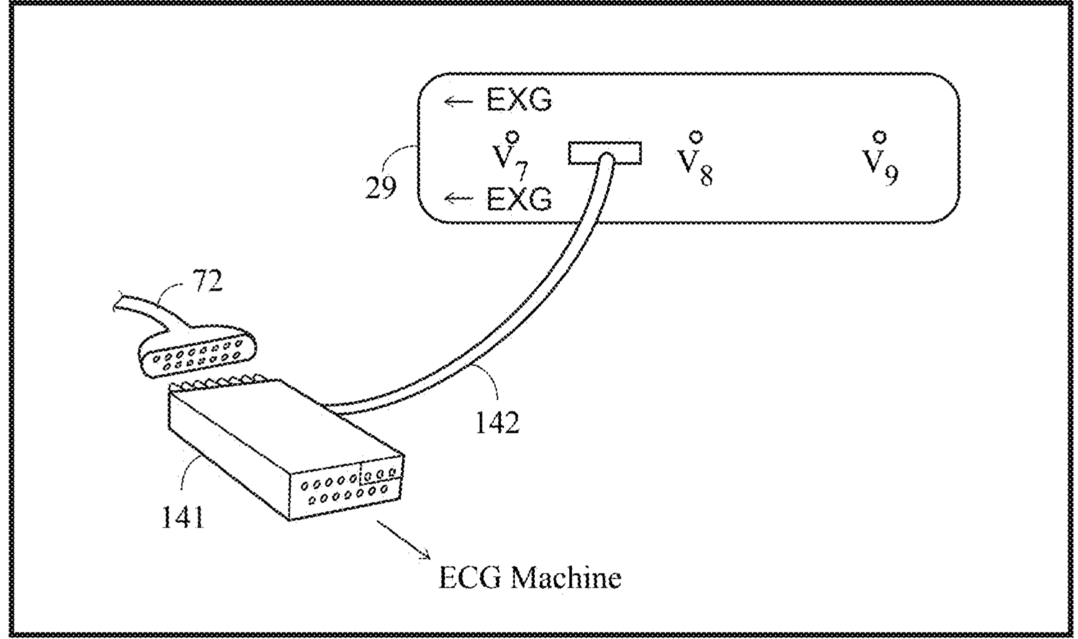
FIG. 14 is an isolated view of a side extension for an emergency cardiac and ECG electrode placement device.

A posterior extension member 29 is shown in FIG. 14. This additional posterior extension member 29 preferably has multiple electrodes that connect via cable 142 to an intermediary adapter module 141 which connects to the electrode connector 72. The posterior leads preferably are connected through the adapter module 141 onto the end of the original EXG device 20 and basically take over leads V5-6 for the standard ECG.

Figure 15A:
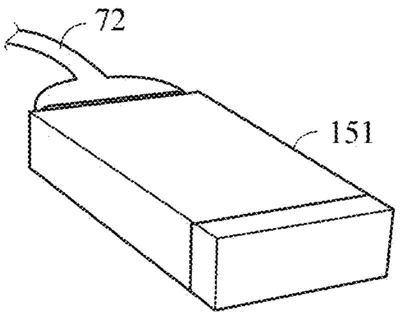
FIG. 15A is an isolated view of a wireless emitter for an emergency cardiac and ECG electrode placement system.
Figure 15B:
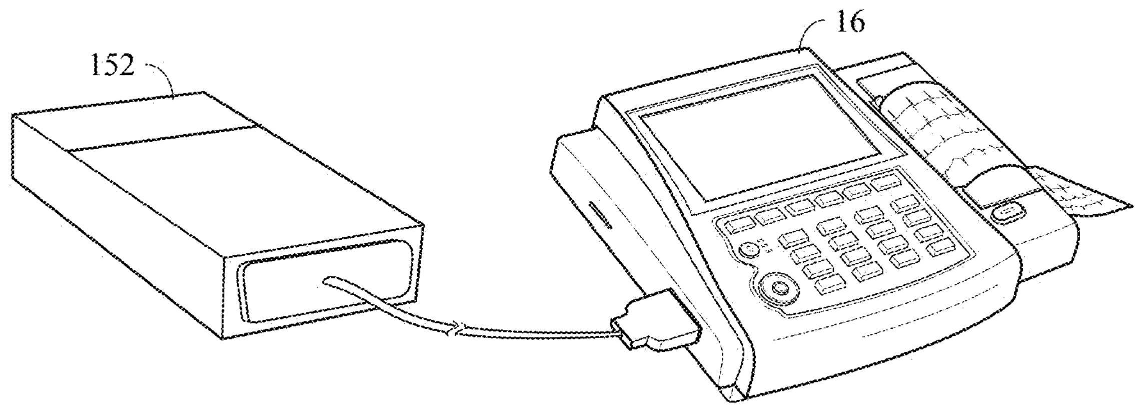
FIG. 15B is an isolated view of a wireless receiver for an emergency cardiac and ECG electrode placement system.

As shown in FIGS. 15A and 15B, in an alternative embodiment, the EXG device 20 comprises a wireless emitter 151 and a wireless receiver 152. The wireless emitter 151 is connected to electrode connector 72, and the wireless receiver is connected to the ECG machine 16. The wireless emitter 151 and the wireless receiver 152 preferably operation on a BLUETOOTH communication protocol.

Figure 16:
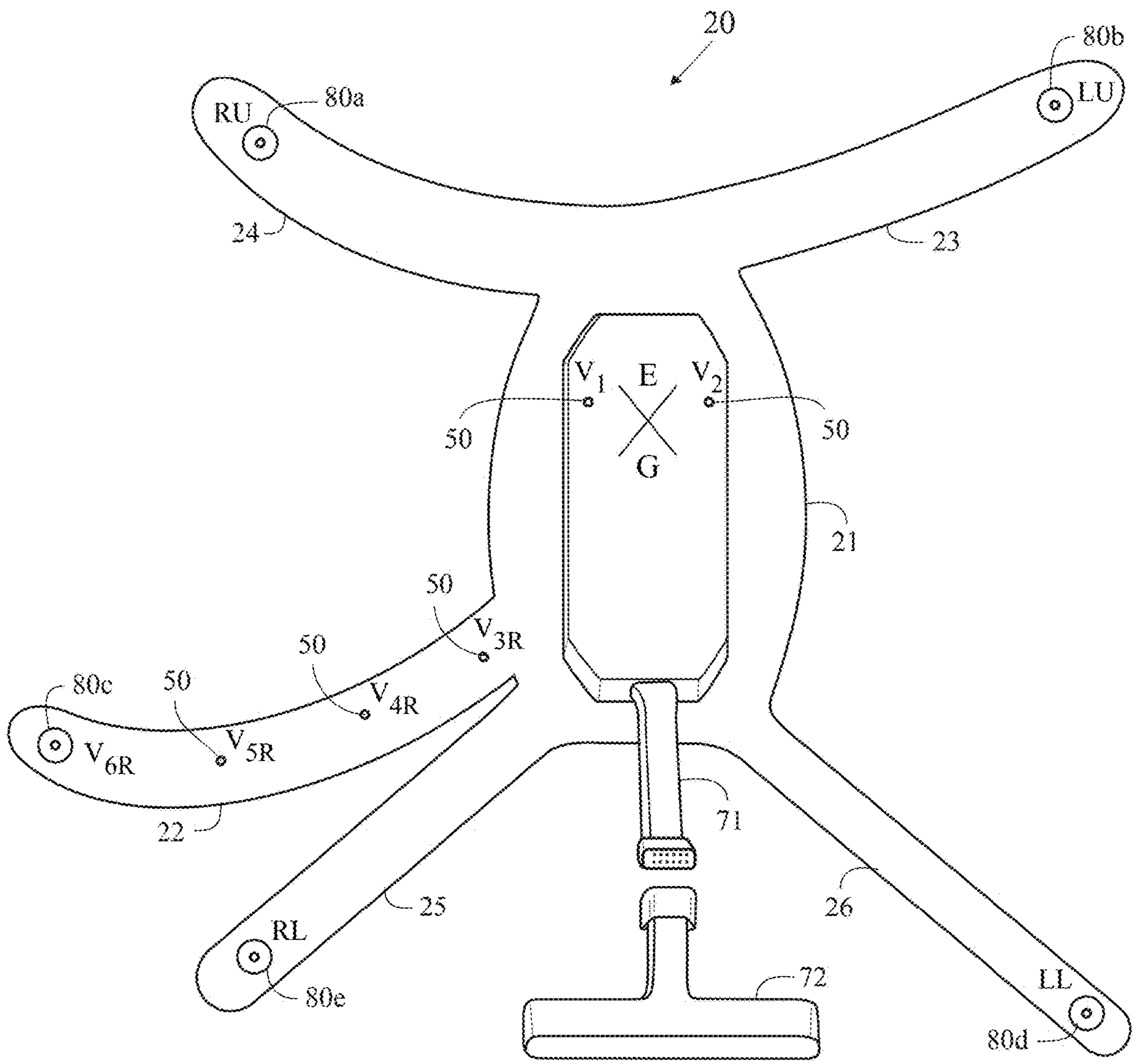
FIG. 16 is a bottom plan view of a second embodiment of an emergency.

As shown in FIG. 16, the EXG device 20 also preferably comprises a plurality of external electrodes 80. A third extension member 24 comprises a first external electrode 80*a*. A second extension member 23 comprises a second external electrode 80*b*. A first extension member 22 comprises a third external electrode 80*c*. A fifth extension member 26 comprises a fourth external electrode 80*d*. A fourth extension member 25 comprises a fifth external electrode 80*e*.

Figure 17:
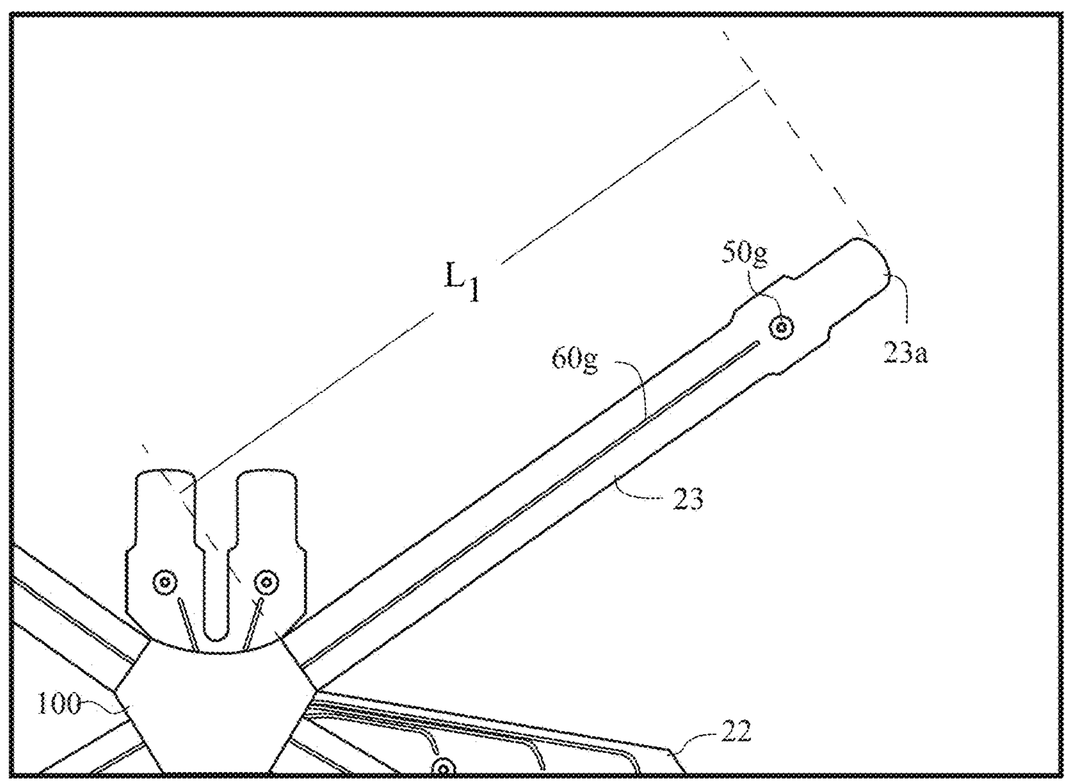
FIG. 17 is an isolated top plan view of a second embodiment of an emergency cardiac and ECG electrode placement device in an application state with an un-extended extension.
Figure 17A:
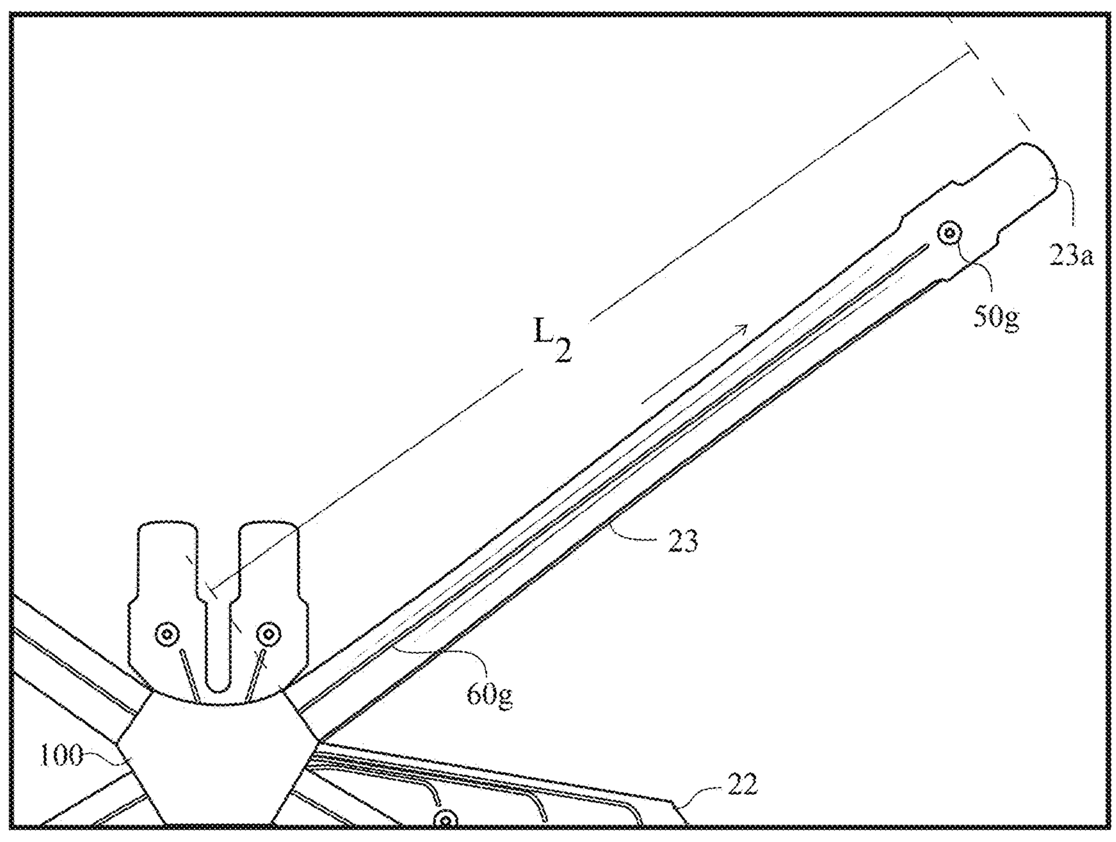
FIG. 17A is an isolated top plan view of a second embodiment of an emergency cardiac and ECG electrode placement device in an application state with an extended extension.

FIGS. 17 and 17A illustrate the stretching capability of the extension members of the EXG device 20. The extension member 23 extends from a length L1 (as shown in FIG. 17) to a length L2 (as shown in FIG. 17A). In a preferred embodiment, each extension member 23, 24, 25 and 26 extends from a length L1 ranging from 7.0 to 14.0 inches to a length L2 ranging from 10.0 to 16.5 inches. In a most preferred embodiment, L1 ranges from 10 to 11 inches, and L2 ranges from 12 to 13 inches. A width of each extension member 22, 23, 24, 25, 26 preferably ranges from 1 centimeter ("cm") to 10 cm, and most preferably 2.5 cm to 5 cm. A thickness of each extension member 22, 23, 24, 25, 26 preferably ranges from 0.1 inch to 0.5 inch.

Figure 18:
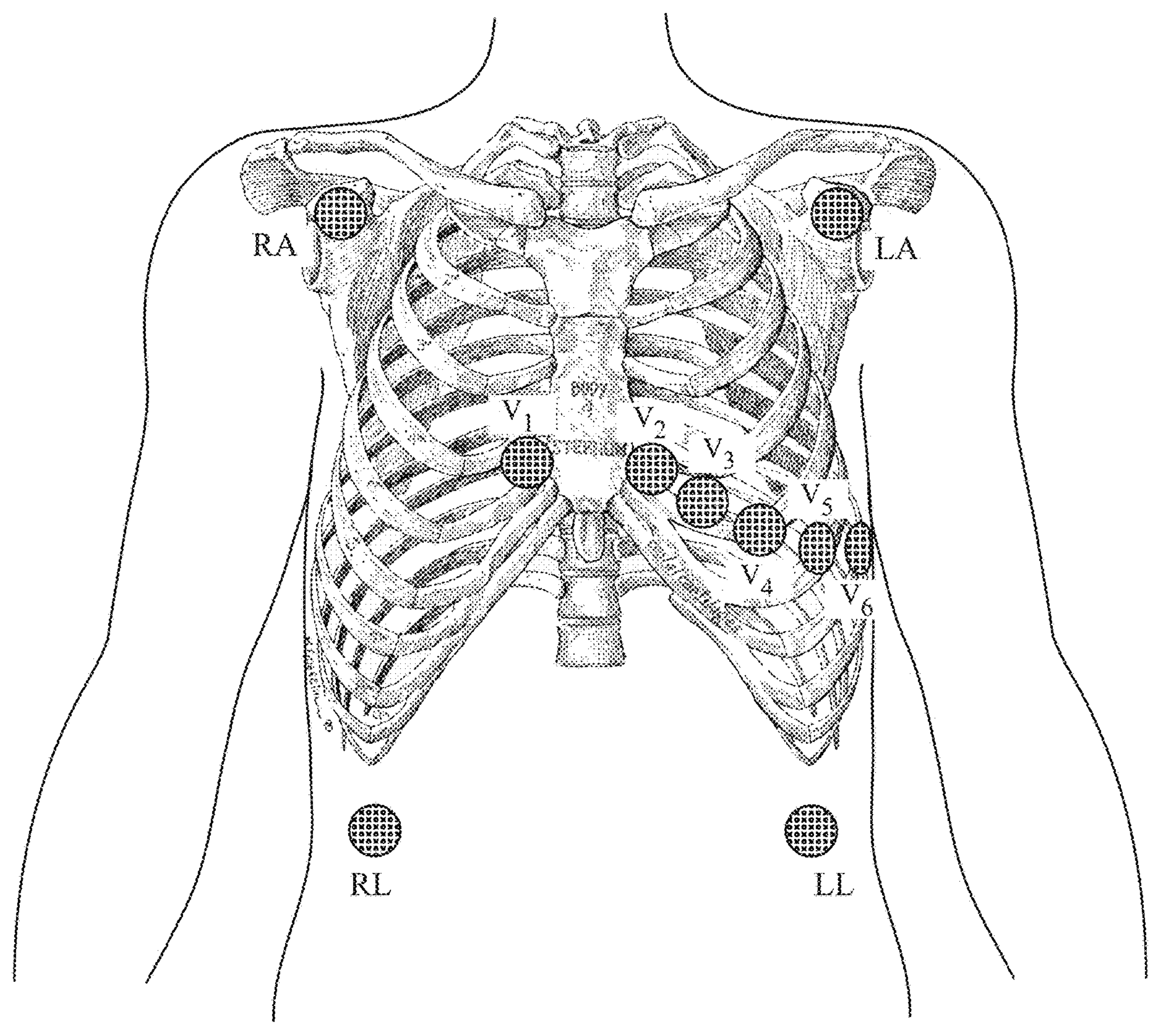
FIG. 18 is an illustration of a human body showing a chest skeleton and markers for electrode placement.
Figure 19:
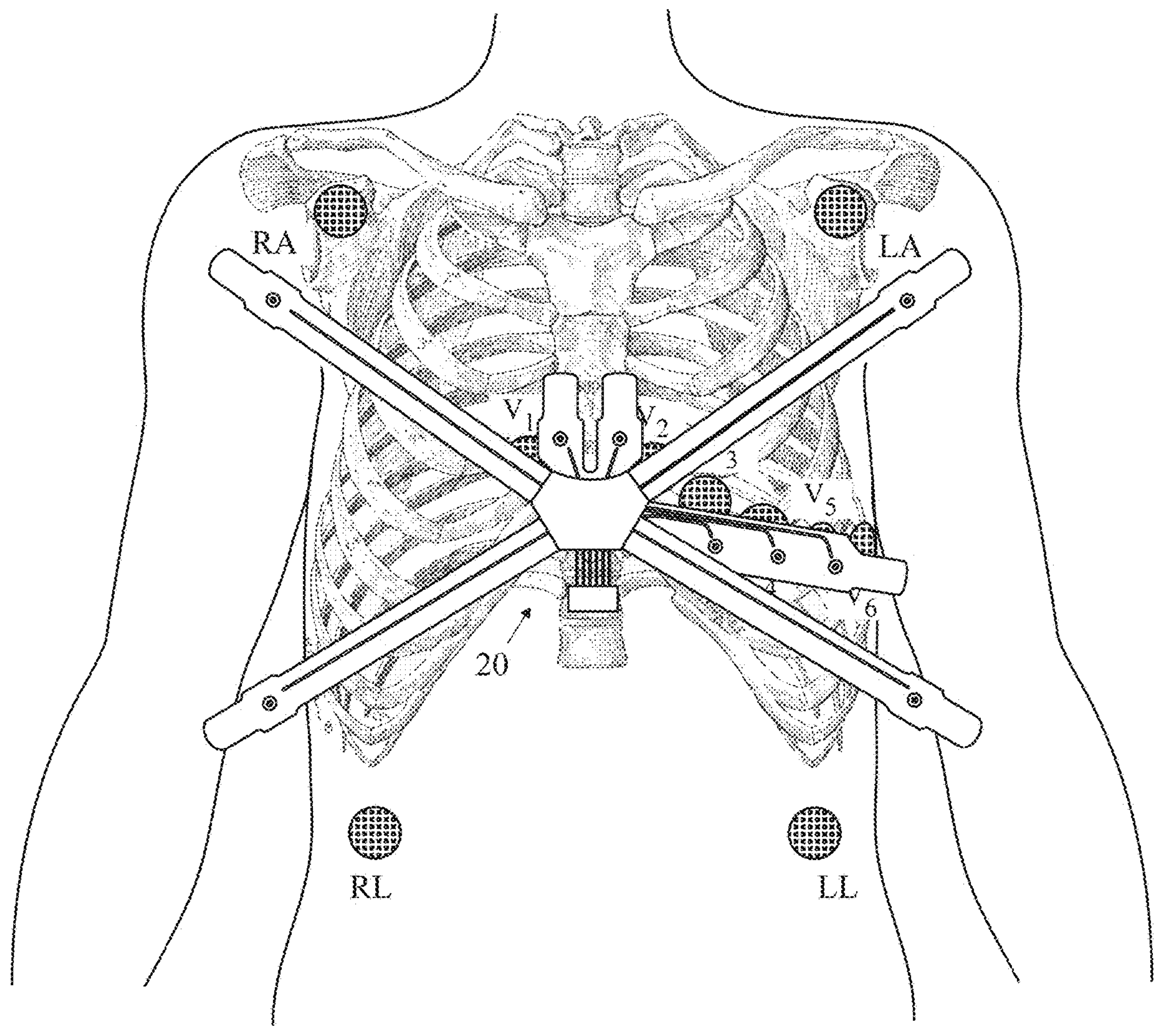
FIG. 19 is an illustration of a human body showing a chest skeleton and markers for electrode placement with an overlay of the emergency cardiac and ECG electrode placement device.

FIG. 18 is an illustration of a human body showing a chest skeleton and markers for electrode placement. FIG. 19 is an illustration of a human body showing a chest skeleton and markers for electrode placement with an overlay of the emergency cardiac and ECG electrode placement device 20.

Figure 20:
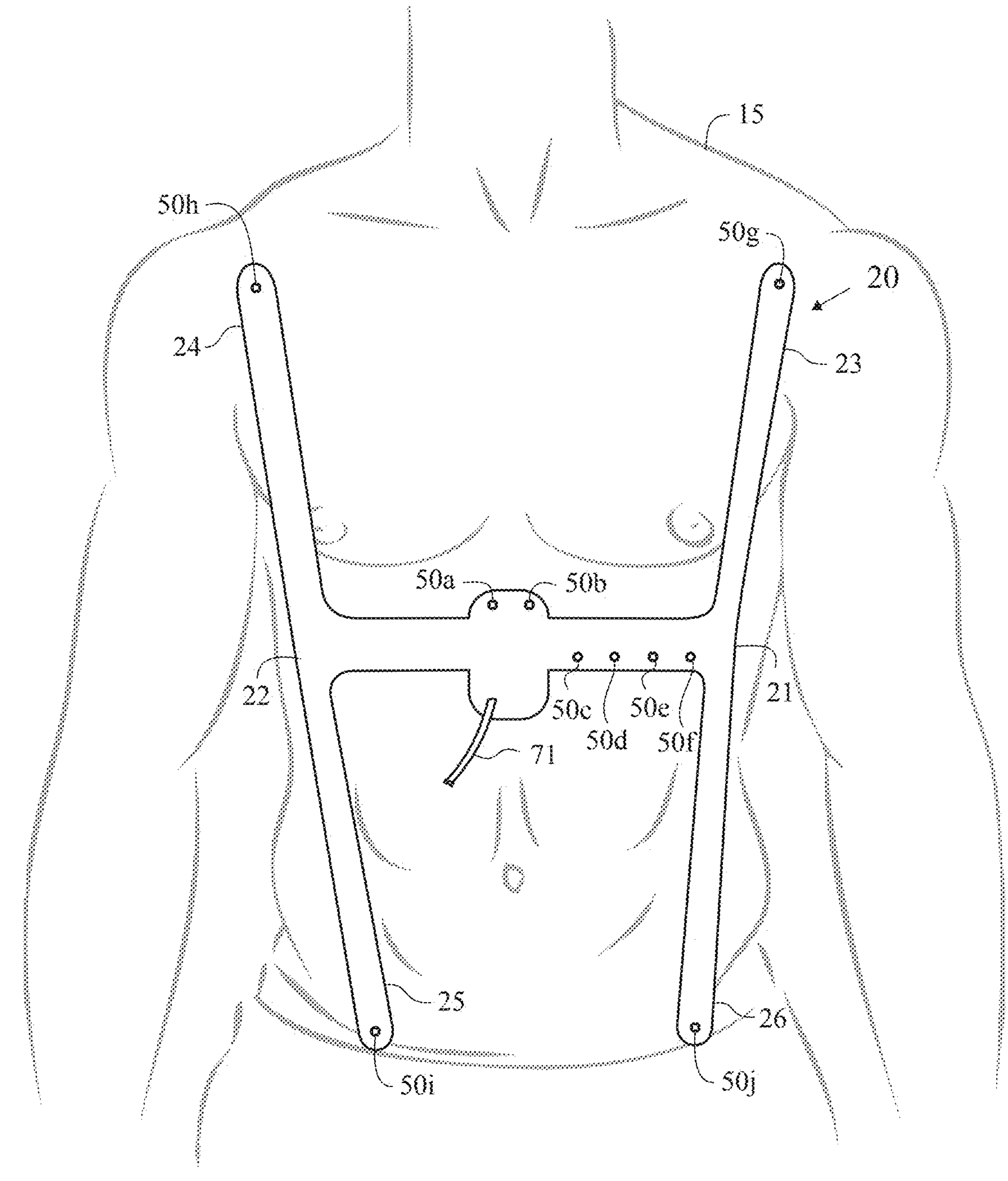
FIG. 20 is an illustration of a first embodiment of an emergency cardiac and ECG electrode placement device positioned on a patient.
Figure 21:
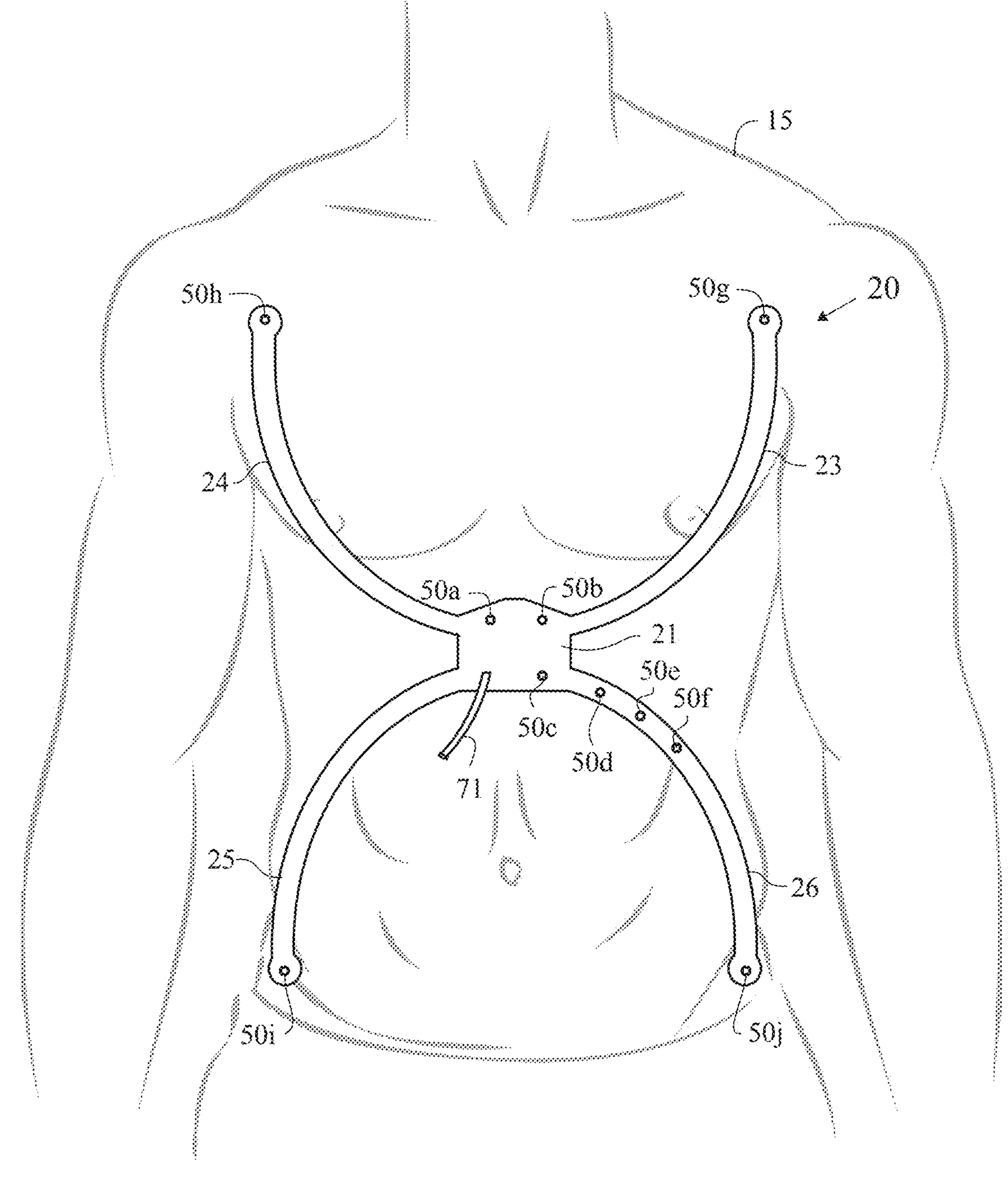
FIG. 21 is an illustration of a second embodiment of an emergency cardiac and ECG electrode placement device positioned on a patient.
Figures 22, 22A, 22B, 22C:
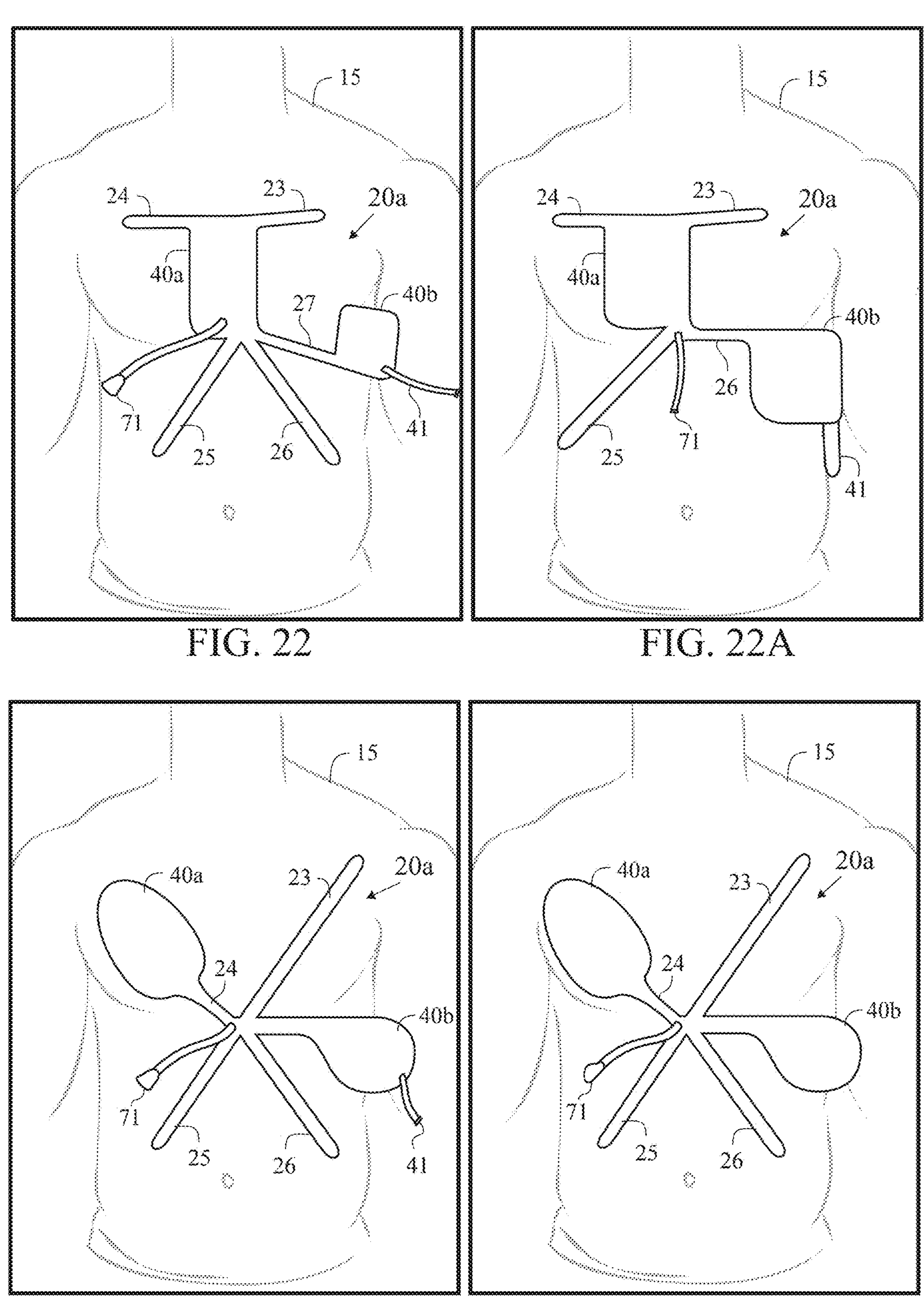
FIG. 22 is an illustration of a third embodiment of an emergency cardiac and ECG electrode placement device with a defibrillation mechanism positioned on a patient.
FIG. 22A is an illustration of a fourth embodiment of an emergency cardiac and ECG electrode placement device with a defibrillation mechanism positioned on a patient.
FIG. 22B is an illustration of a fifth embodiment of an emergency cardiac and ECG electrode placement device with a defibrillation mechanism positioned on a patient.
FIG. 22C is an illustration of a sixth embodiment of an emergency cardiac and ECG electrode placement device with a defibrillation mechanism positioned on a patient.
Figures 23, 23A, 23B, 23C:
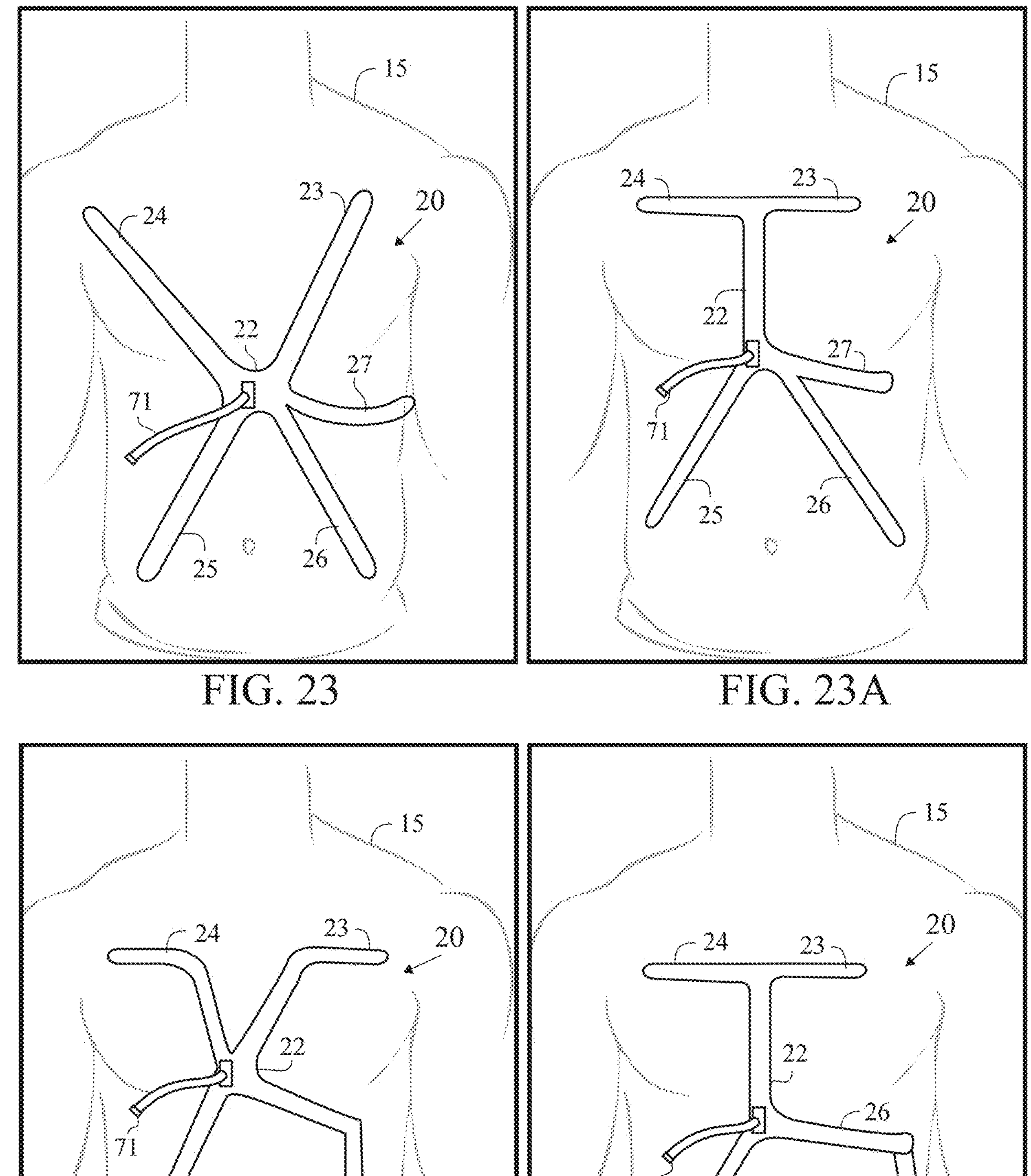
FIG. 23 is an illustration of a seventh embodiment of an emergency cardiac and ECG electrode placement device positioned on a patient.
FIG. 23A is an illustration of an eighth embodiment of an emergency cardiac and ECG electrode placement device positioned on a patient vice.
FIG. 23B is an illustration of a ninth embodiment of an emergency cardiac and ECG electrode placement device positioned on a patient.
FIG. 23C is an illustration of a tenth embodiment of an emergency cardiac and ECG electrode placement device positioned on a patient.
Figures 24, 24A:
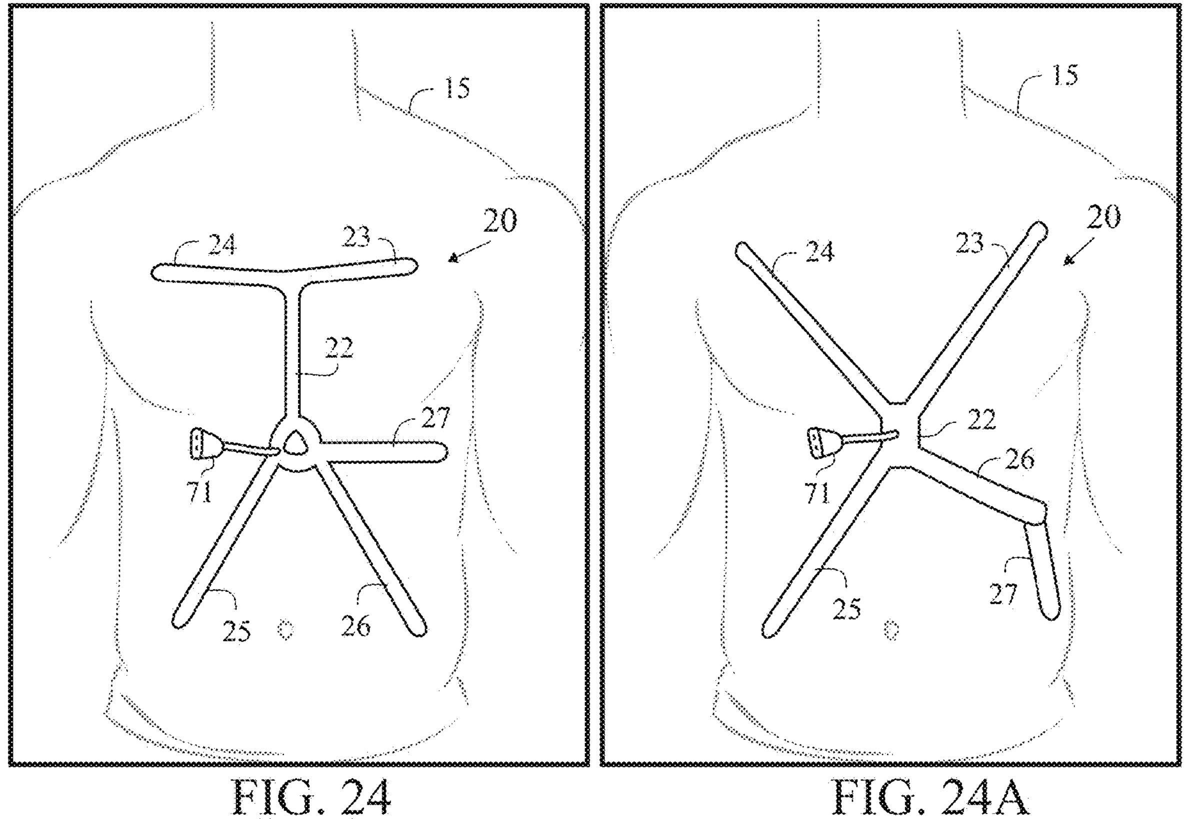
FIG. 24 is an illustration of an eleventh embodiment of an emergency cardiac and ECG electrode placement device positioned on a patient.
FIG. 24A is an illustration of a twelfth embodiment of an emergency cardiac and ECG electrode placement device positioned on a patient.

As shown in FIGS. 20 and 21, the EXG device 20 preferably comprises a body 21, electrodes 50, printed wires or an electrical conducting flexible material 60 (not shown), and an electrode cable connector 71. The body 21 preferably comprises a center extension member 22, a first extension member 23, a second extension member 24, a third extension member 25 and a fourth extension member 26. The electrode cable connector 71 is positioned on the body 21. Each extension member 22-26 preferably has a width ranging from 1 cm to 10 cm, and a length ranging from 5 cm to 20 cm. The center extension member 22 preferably comprises a first electrode 50*a*, a second electrode 50*b*, a third electrode 50*c*, a fourth electrode 50*d*, a fifth electrode 50*e* and a sixth electrode 50*f*. Printed wires or electrical conducting flexible material 60 (not shown) connect each electrode 50 to the electrode cable connector 71.

Other embodiments of EXG device 20 are shown in FIGS. 23, 23A, 23B, 23C, 24 and 24A. The extension members extend outward from the center of the body 21.

Figure 29:
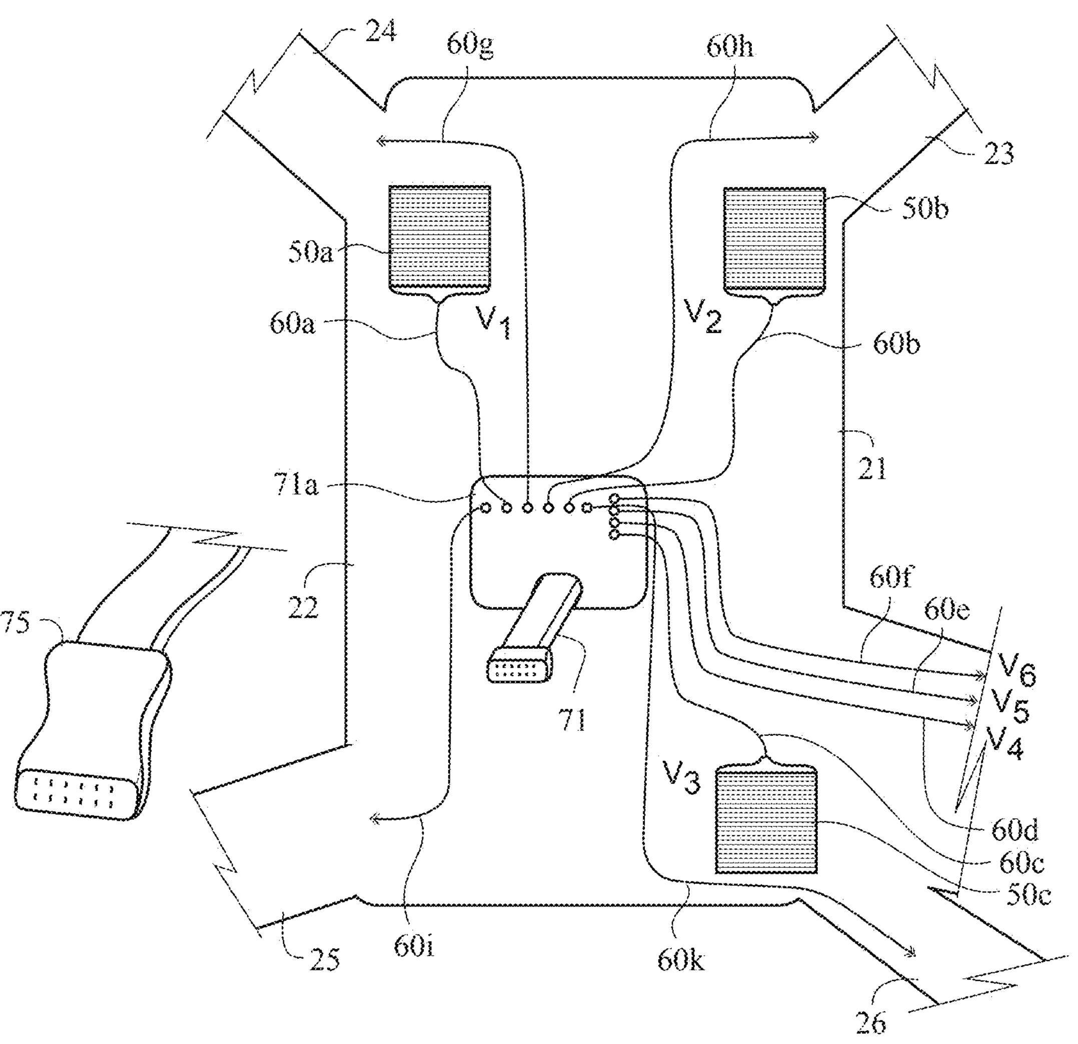
FIG. 29 is an isolated view of a portion of an emergency cardiac and ECG electrode placement device.

As shown in FIG. 29, a printed wire 60*a* connects the electrode 50*a* to the electrode cable connector 71. A printed wire 60*b* connects the electrode 50*b* to the electrode cable connector 71. A printed wire 60*c* connects the electrode 50*c* to the electrode cable connector 71. A printed wire 60*d* connects the electrode 50*d* to the electrode cable connector 71. A printed wire 60*e* connects the electrode 50*e* to the electrode cable connector 71. A printed wire 60*f* connects the electrode 50*f* to the electrode cable connector 71. A printed wire 60*g* connects the electrode 50*g* to the electrode cable connector 71. A printed wire 60*h* connects the electrode 50*h* to the electrode cable connector 71. A printed wire 60*i* connects the electrode 50*i* to the electrode cable connector 71. A printed wire 60*j* connects the electrode 50*j* to the electrode cable connector 71. A ten pin electrode interface 75 connects to the electrode cable connector 71. On one embodiment, the elastic electrically conductive material is preferably applied with a 3D printer directly on the main layer.

Alternatively, an elastic conductive material is substituted for each of the printed wires in FIG. 29. Such elastic conductive materials preferably comprise silver chloride and/or graphene. The body 21 is preferably composed of a kinesiology type tape.

Alternative embodiments of the EXG device 20*a* shown in FIGS. 22, 22A, 22B, and 22C also comprise integrated defibrillation pads 40*a* and 40*b* connected to a defibrillation cable 41. In the unstable patient, defibrillation becomes a crucial aspect of emergency cardiac care. The use of defibrillation pads has in the field historically been done with pad placement at the discretion of the first responder/paramedic. The most common deployment being anteriorly. This often leads to suboptimal placement and suboptimal delivery of electricity. The EXG-DF with defibrillator pad assures proper placement of the device in the anterior posterior configuration, which allows for optimal electrical conductance to the heart. The vector of electrical conductance is optimally placed in an anterior posterior configuration. There is no device that provides optimal defibrillator pad placement while integrating twelve lead EKG ability with ability to extend to include posterior and right sided lead EKG. The ability to obtain instant EKG data after critical defibrillation has heretofore been impractical for the pre-hospital care provider. The EXG-DF-DF addresses this critical issue in cardiac care.

Figure 25:
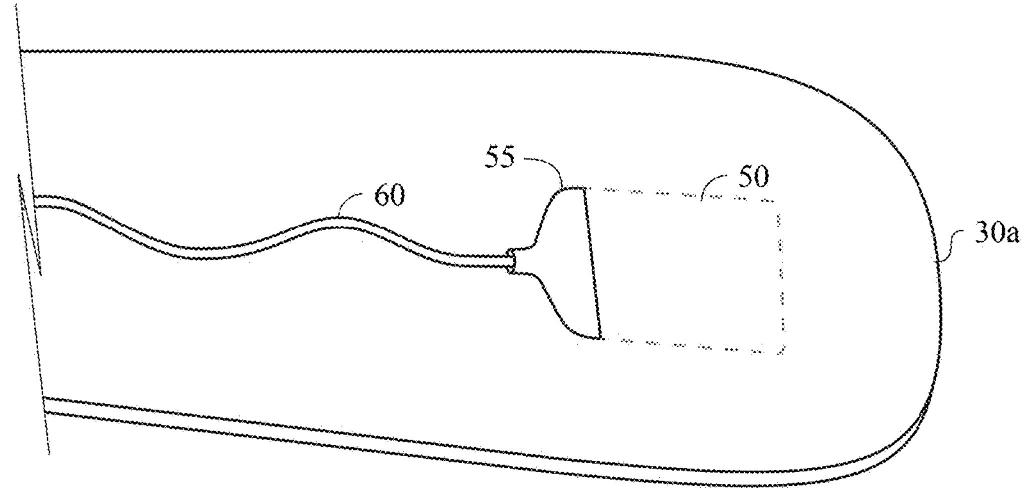
FIG. 25 is an isolated top perspective view of a top surface of an extension of an emergency cardiac and ECG electrode placement device.

FIG. 25 illustrates an isolated top perspective view of a top surface of an extension of the EXG device 20. The extension has a top layer 30*a* with an integrated printed wire (or elastic electrical conducting material) 60 connected to an electrode interface 55 integrated with an electrode 50 that is positioned on an adhesive surface below. The electrode 50 is not positioned on the top surface 30*a* of the main layer 30.

Figure 26:
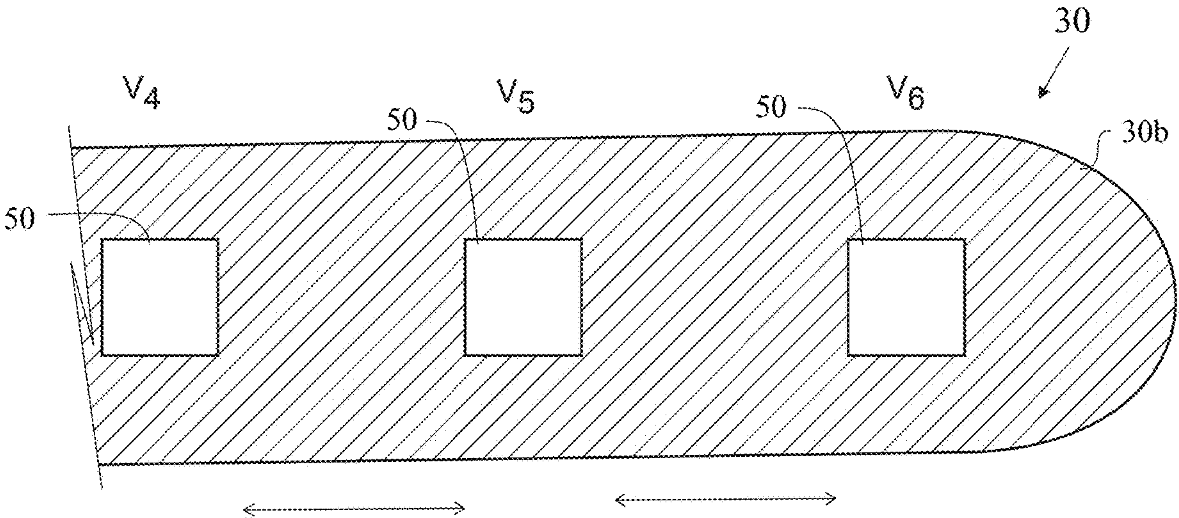
FIG. 26 is an isolated bottom plan view of a bottom surface of an extension of an emergency cardiac and ECG electrode placement device.

FIG. 26 illustrates an isolated bottom plan view of a bottom surface of an extension of an EXG device 20. On bottom adhesive surface 30*b* of the main layer 30 has electrodes 50 positioned thereon.

Figure 27:
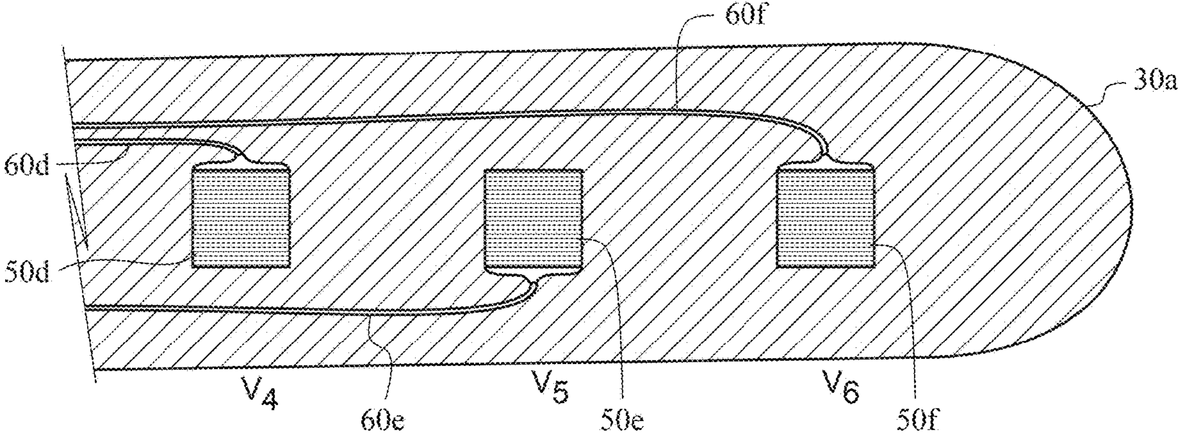
FIG. 27 is an isolated top plan view of a top surface of an extension of an emergency cardiac and ECG electrode placement device.

FIG. 27 illustrates an isolated top plan view of a top surface of an extension of the EXG device 20. The main layer 30 of the extension has a top layer 30*a* with an integrated printed wires (or elastic electrical conducting material) 60*d*, 60*e* and 60*f* connected to corresponding electrodes 50*d*, 50*e* and 50*f* that are positioned on an adhesive surface below. The electrodes 50*d*, 50*e* and 50*f* are not positioned on the top surface 30*a* of the main layer 30.

Figure 28:
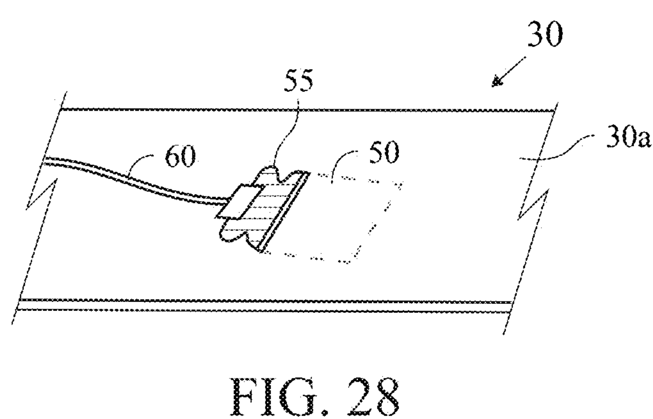
FIG. 28 is an isolated top perspective view of a top surface of an extension of an emergency cardiac and ECG electrode placement device.
Figure 28A:
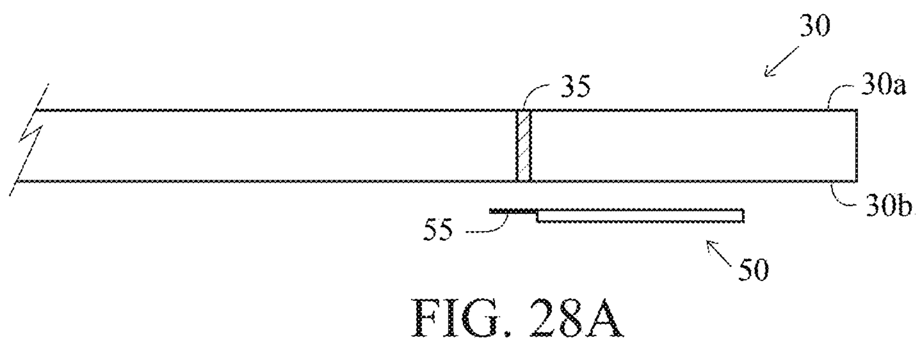
FIG. 28A is an isolated exploded cross-sectional view of the extension of an emergency cardiac and ECG electrode placement device of FIG. 28 and an electrode.
Figure 28B:
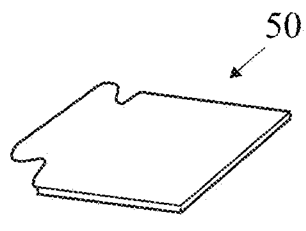
FIG. 28B is an isolated bottom view of an electrode for an emergency cardiac and ECG electrode placement device.
Figure 28C:
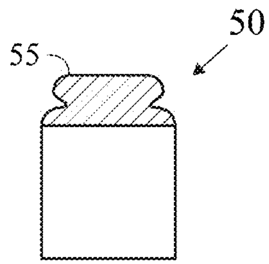
FIG. 28C is an isolated top view of an electrode for an emergency cardiac and ECG electrode placement device.

FIG. 28 is an isolated top perspective view of a top surface of an extension of the EXG device 20. The extension has a top layer 30*a* with an integrated printed wire (or elastic electrical conducting material) 60 connected to an electrode interface 55 integrated with an electrode 50 that is positioned on an adhesive surface below. The electrode 50 is not positioned on the top surface 30*a* of the main layer 30. FIG. 28A is an isolated exploded cross-sectional view of the extension of the EXG device 20 of FIG. 28 and an electrode 50. The interface 55 is placed through an aperture 35 in the main layer 30 to connect to the integrated printed wire (or elastic electrical conducting material) 60. FIG. 28B is an isolated bottom view of an electrode 50 for an EXG device 20. FIG. 28C is an isolated top view of an electrode 50 with an interface 55 for an EXG device 20. The interface is preferably composed of a conductive material such as graphene or silver chloride. The electrode 50 is preferably composed of a silver chloride material.

Figure 30:
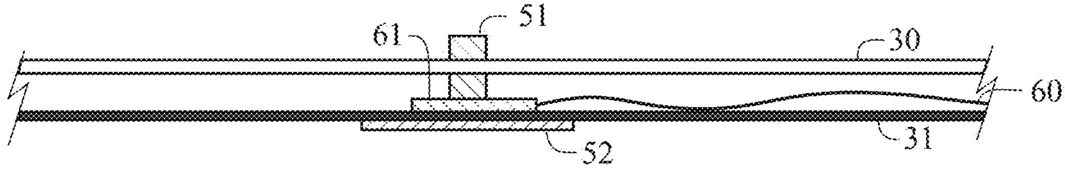
FIG. 30 is an isolated cross-sectional view of an bi-layer extension of with an electrode of a device.
Figure 30A:
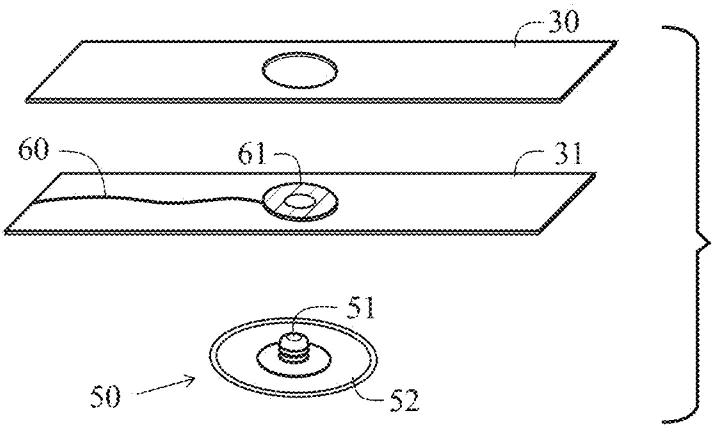
FIG. 30A is an exploded view of FIG. 30.

A bi-layer extension is shown in FIGS. 30 and 30A. Each extension member of the body 21 preferably comprises a top layer 30 composed of a flexible material and an adhesive layer 31 composed of a flexible material, with a removable backing layer attached to an adhesive surface of the adhesive layer 31. A top surface of the adhesive layer preferably includes an integrated printed wire (or elastic electrical conducting material) 60 with a connector 61. One preferred material for the flexible material is KT TAPE from Spidertech. The top layer 30 preferably has a Shore A hardness ranging from 50 to 90, which better allows for chest compressions. One preferred material for the adhesive layer is an adhesive from 3M. Each of the electrodes 50 preferably comprises a connection stud 51 and a contact pad 52. Each contact pad 52 is preferably has a diameter ranging from 30 milliimters ("mm") to 40 mm, and most preferably 35 mm, to in one embedment allow for retention of a gel protector. Each contact pad 52 is preferably composed of a material from 3M. A cable connector 61 is connected to a connection stud 51 of each electrode 50 preferably using a conductive epoxy. Each cable connector 61 is preferably composed of 0.2 mm thick copper, with a 26 mm inside diameter.

Figure 31:
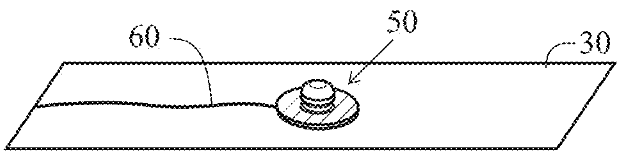
FIG. 31 is an isolated cross-sectional view of a single layer extension of with an electrode of a device.
Figure 31A:
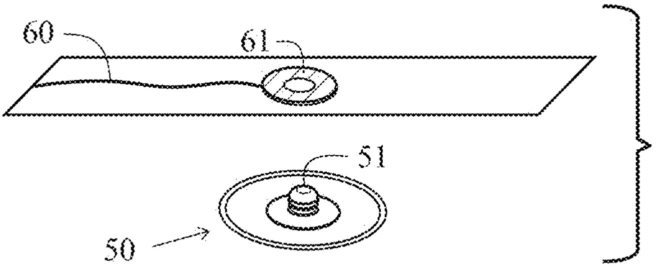
FIG. 31A is an exploded view of FIG. 31.
Figure 32:
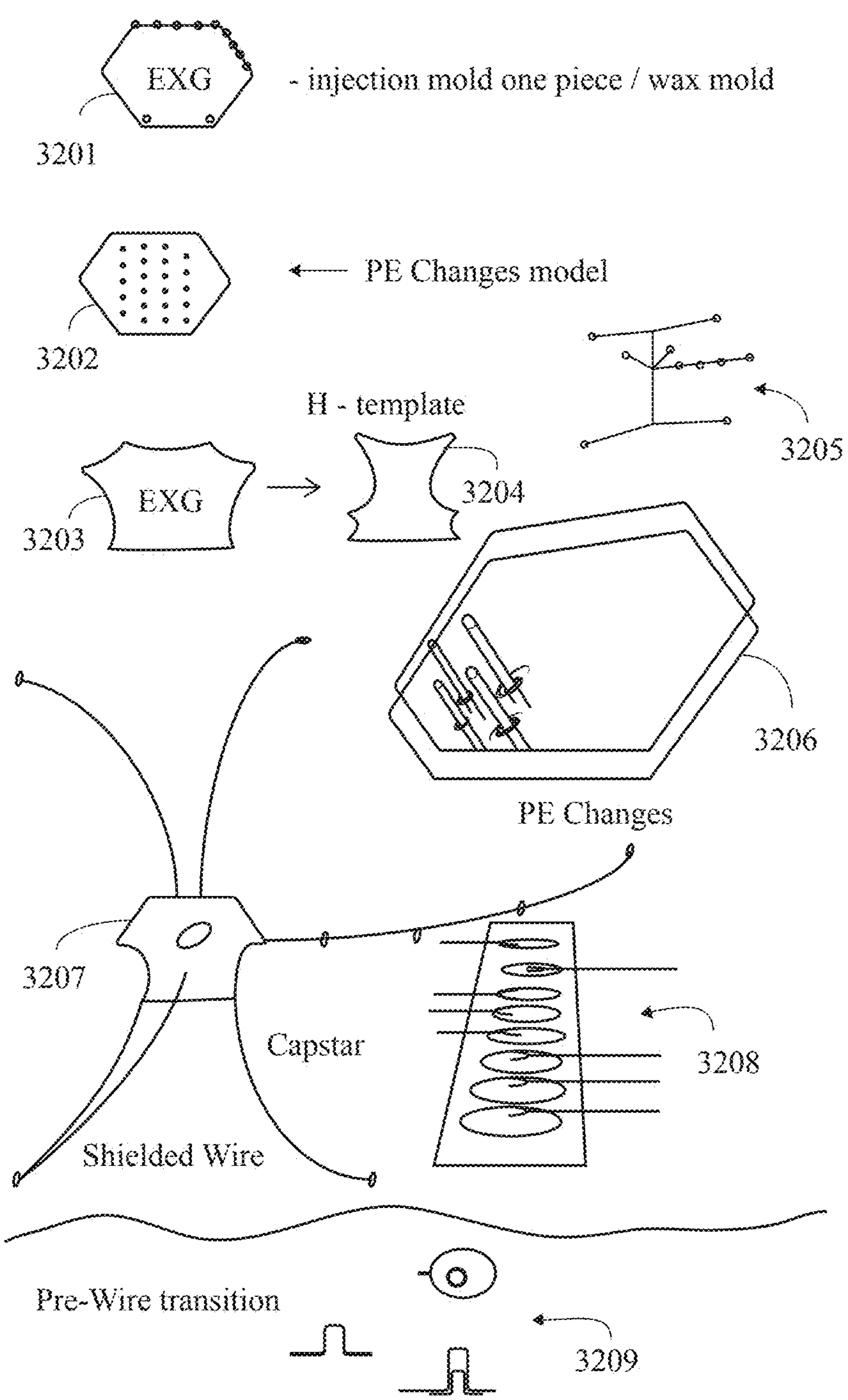
FIG. 32 is an image for an ergonomic cardiac and ECG electrode system.
Figure 33:
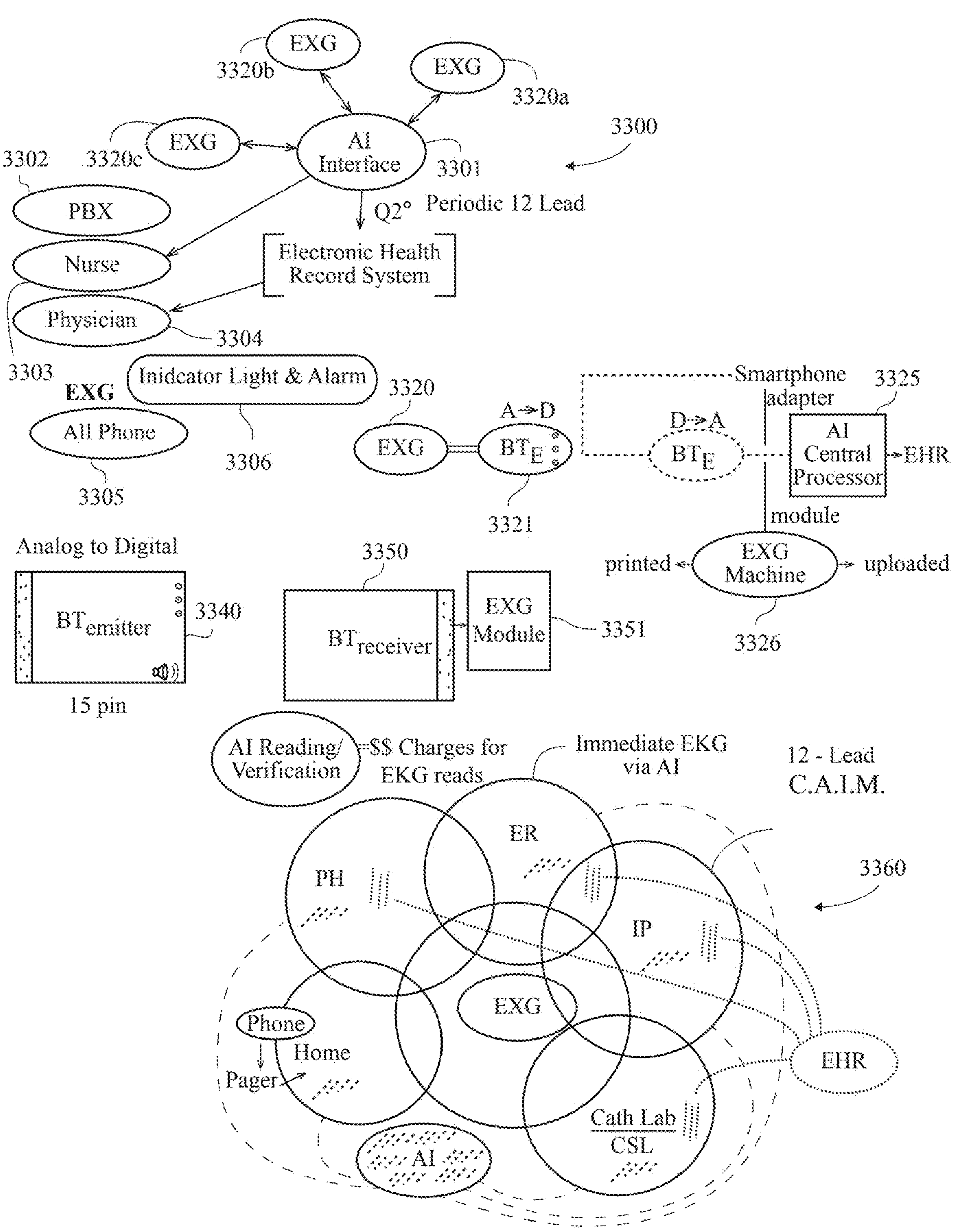
FIG. 33 is an image for an ergonomic cardiac and ECG electrode system.
Figure 33:
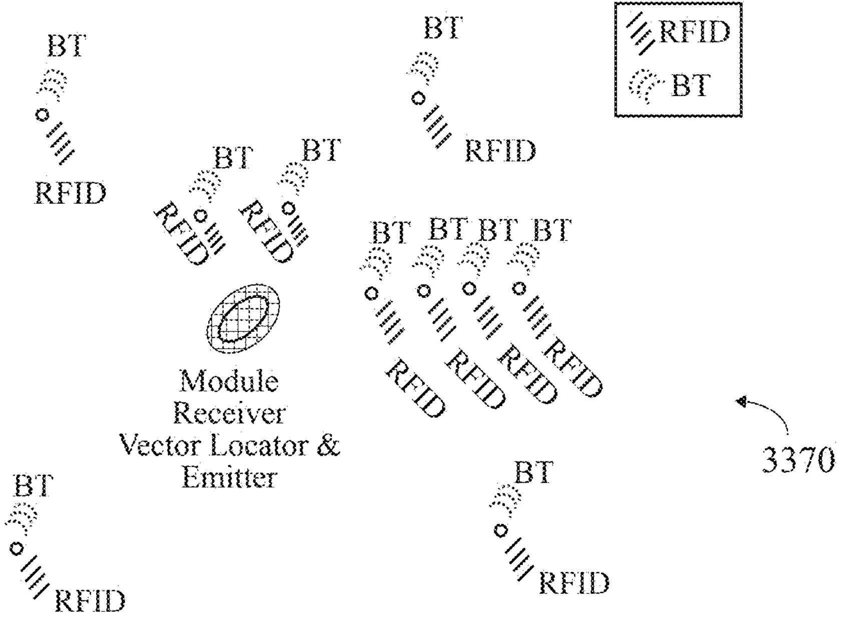
Figure 34:
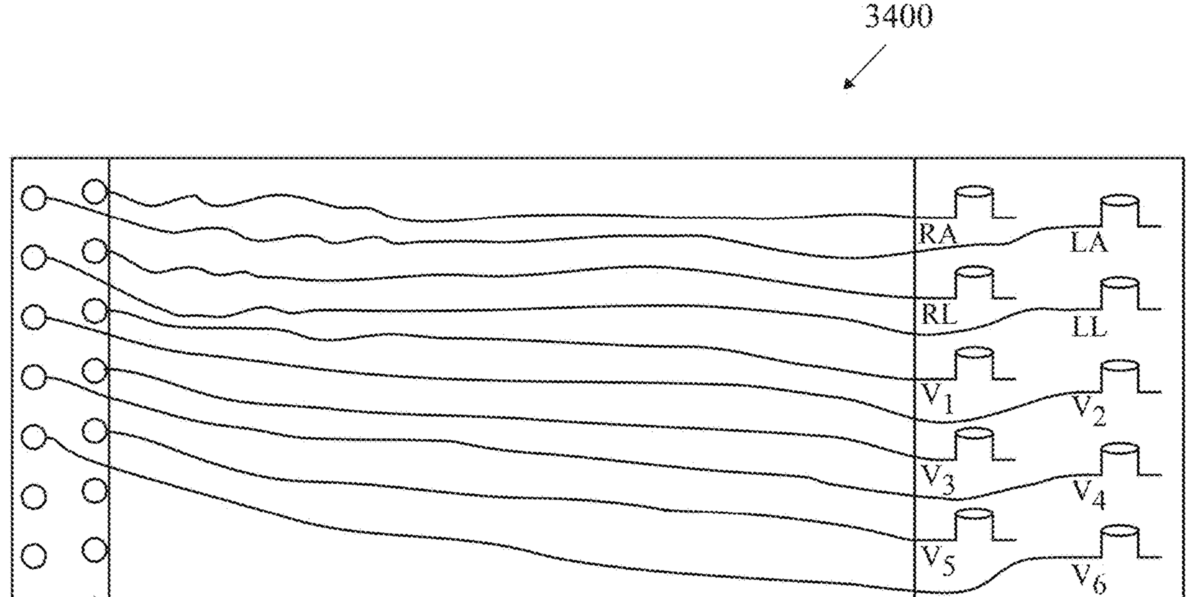
FIG. 34 is an image for an ergonomic cardiac and ECG electrode system.
Figure 35:
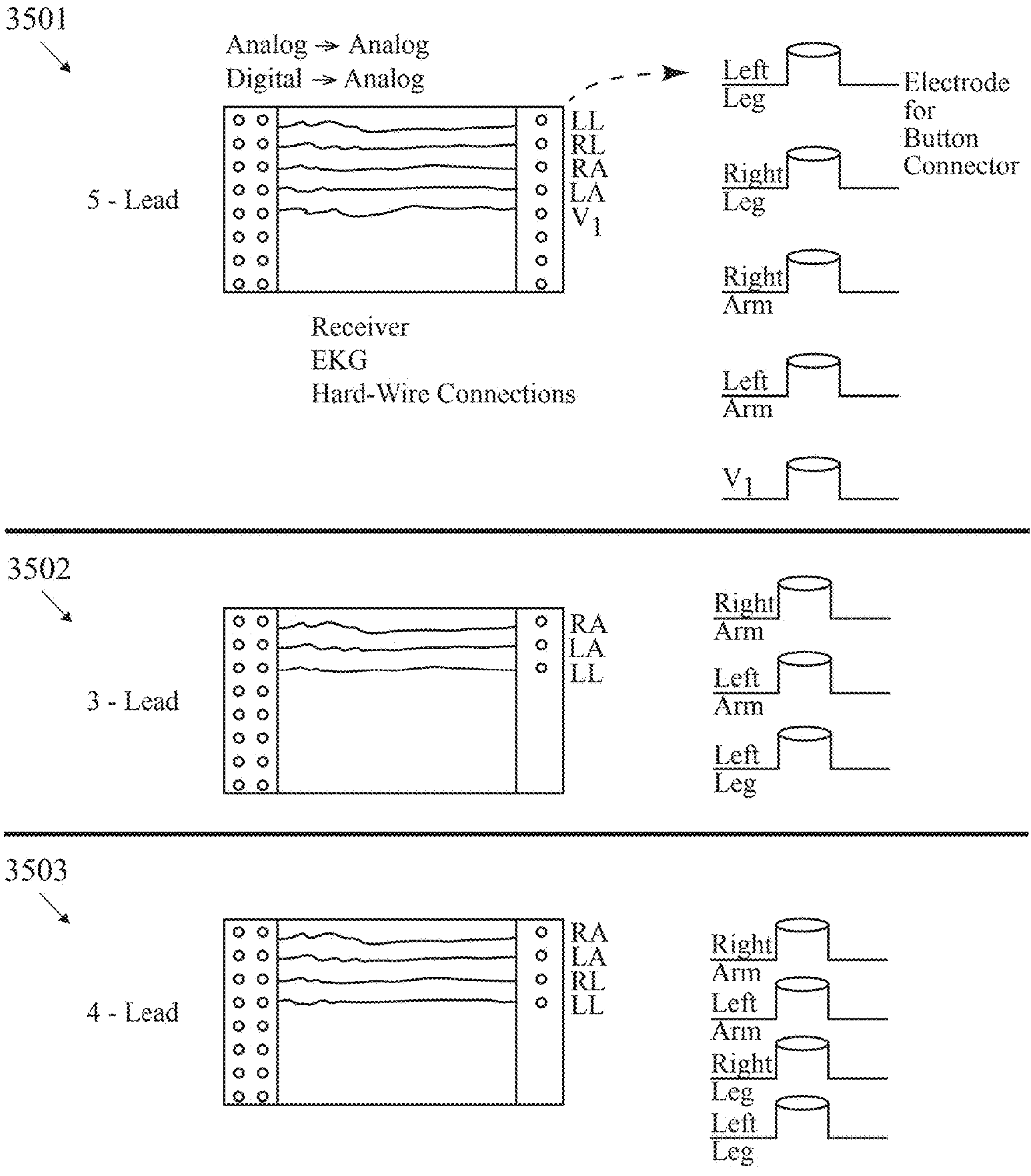
FIG. 35 is an image for an ergonomic cardiac and ECG electrode system.
Figure 36:
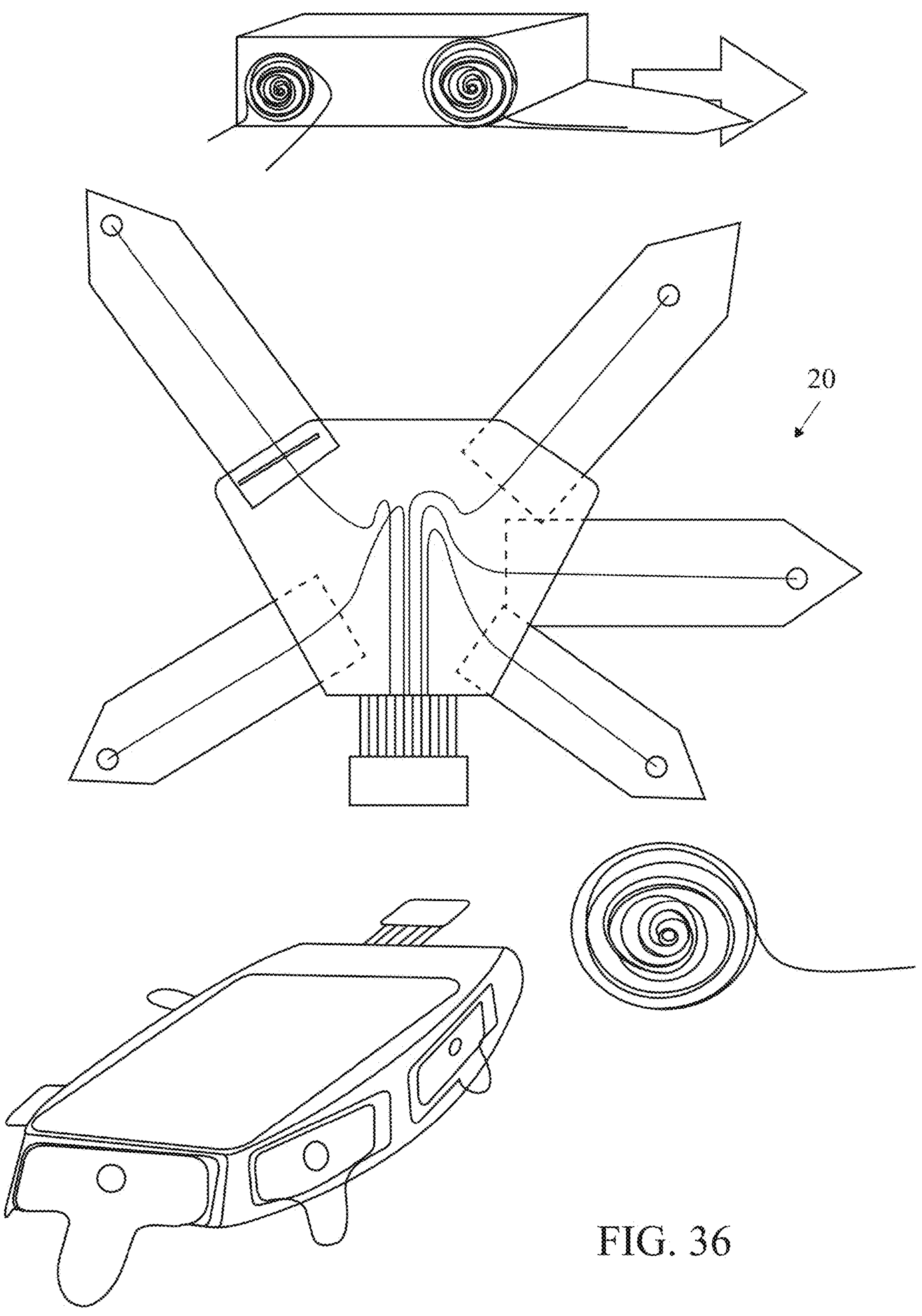
FIG. 36 is an image for an ergonomic cardiac and ECG electrode system.
Figure 37:
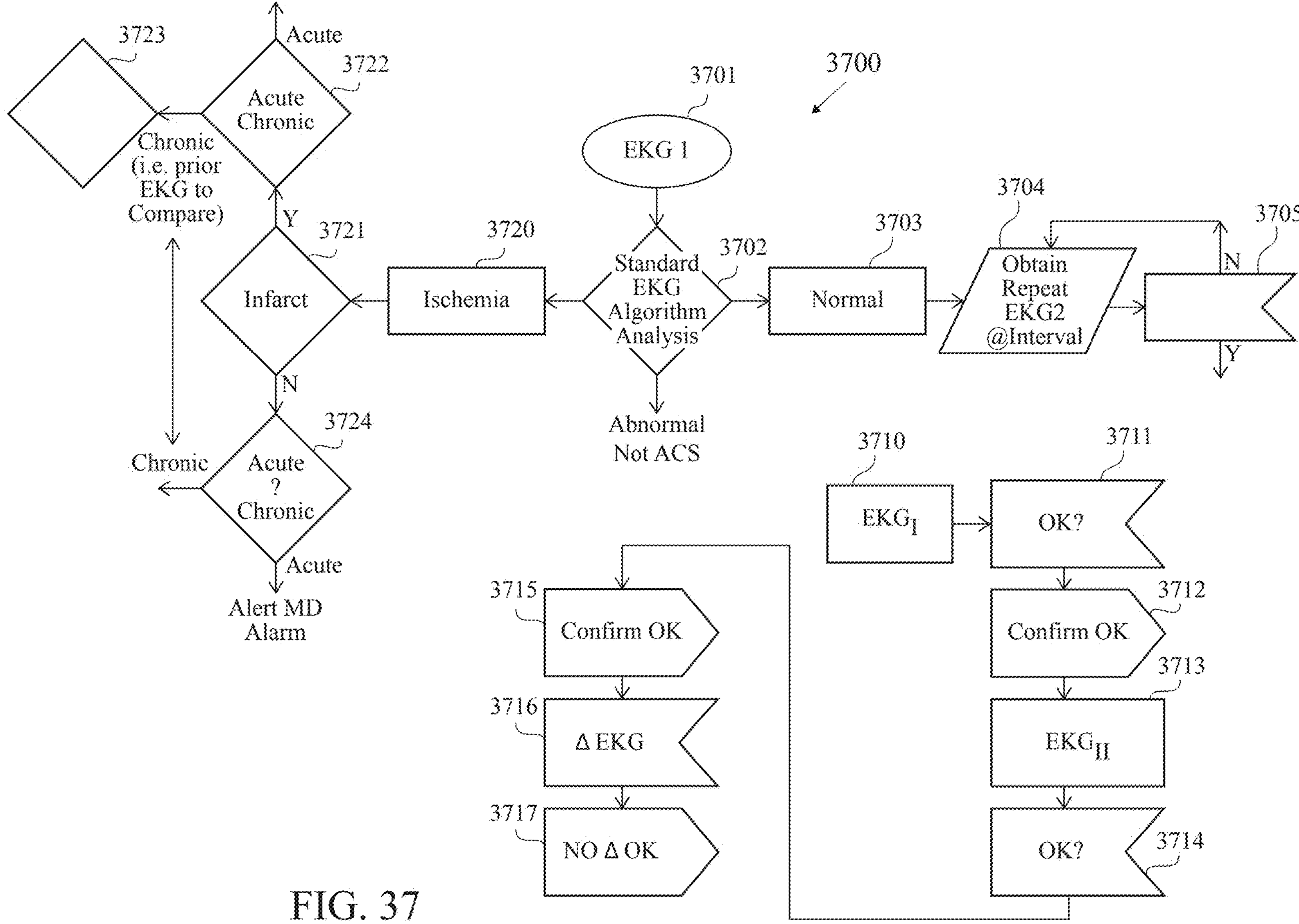
FIG. 37 is an image for an ergonomic cardiac and ECG electrode system.
Figure 38:
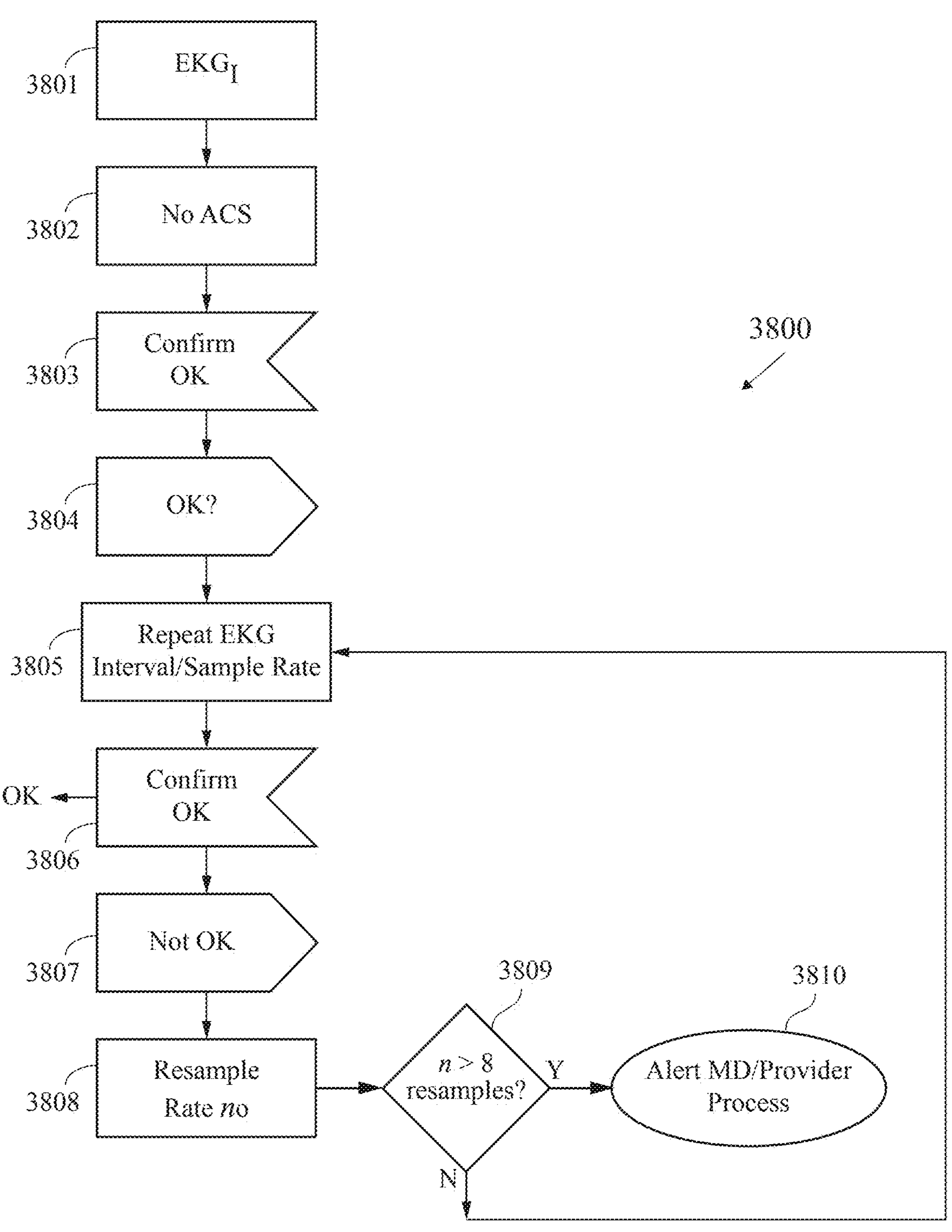
FIG. 38 is an image for an ergonomic cardiac and ECG electrode system.
Figure 39:
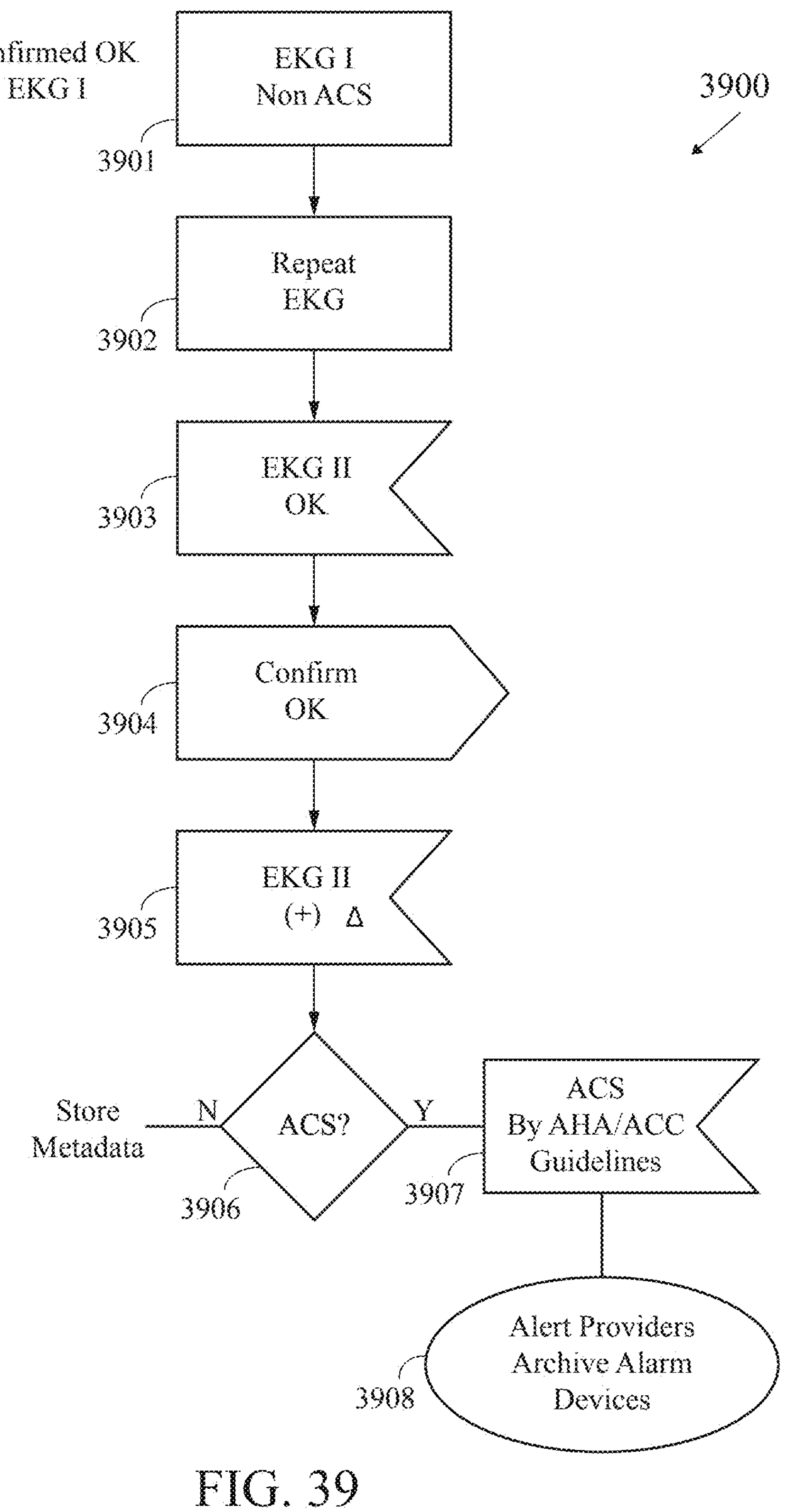
FIG. 39 is an image for an ergonomic cardiac and ECG electrode system.
Figure 40:
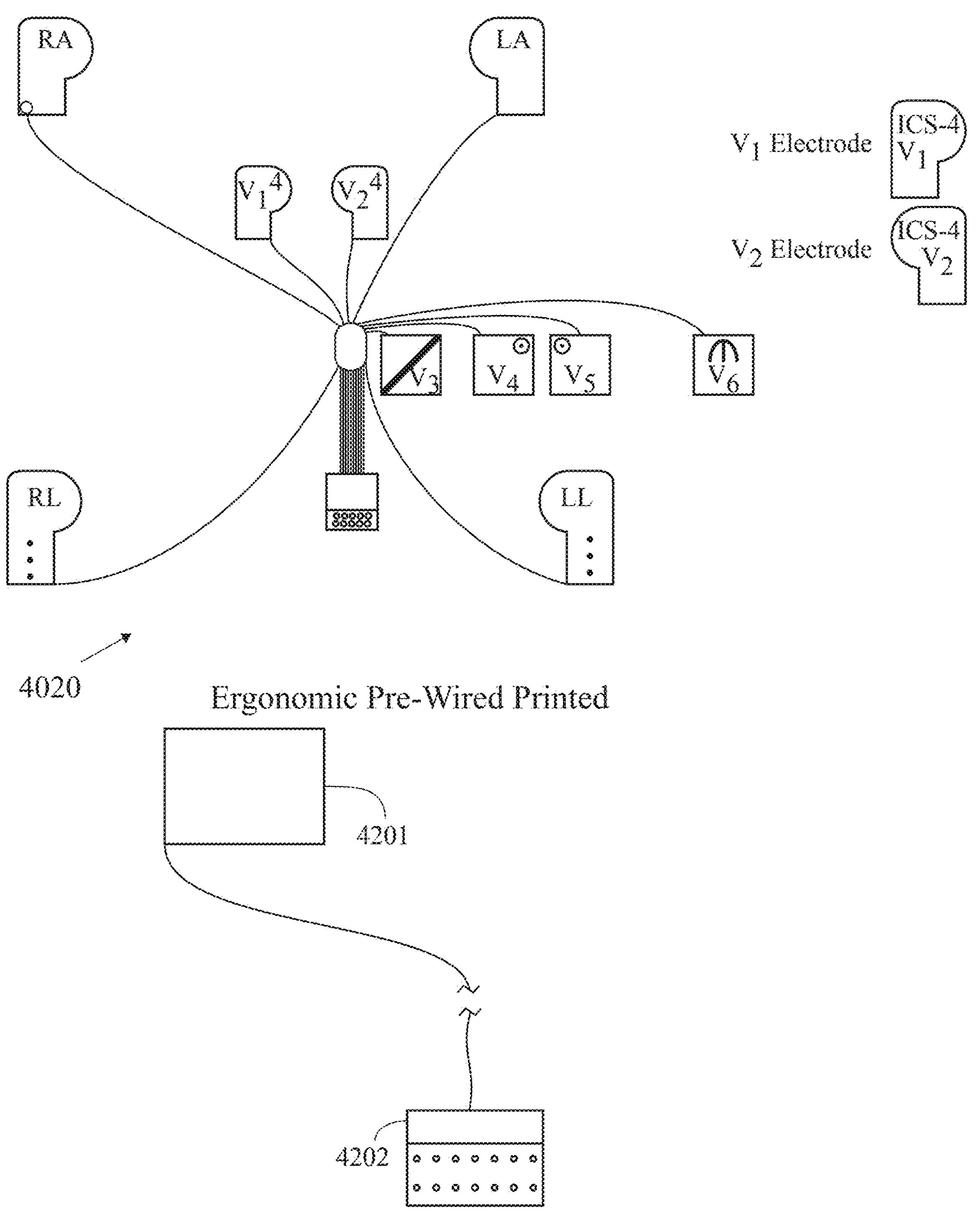
FIG. 40 is an image for an ergonomic cardiac and ECG electrode system.
Figure 41:
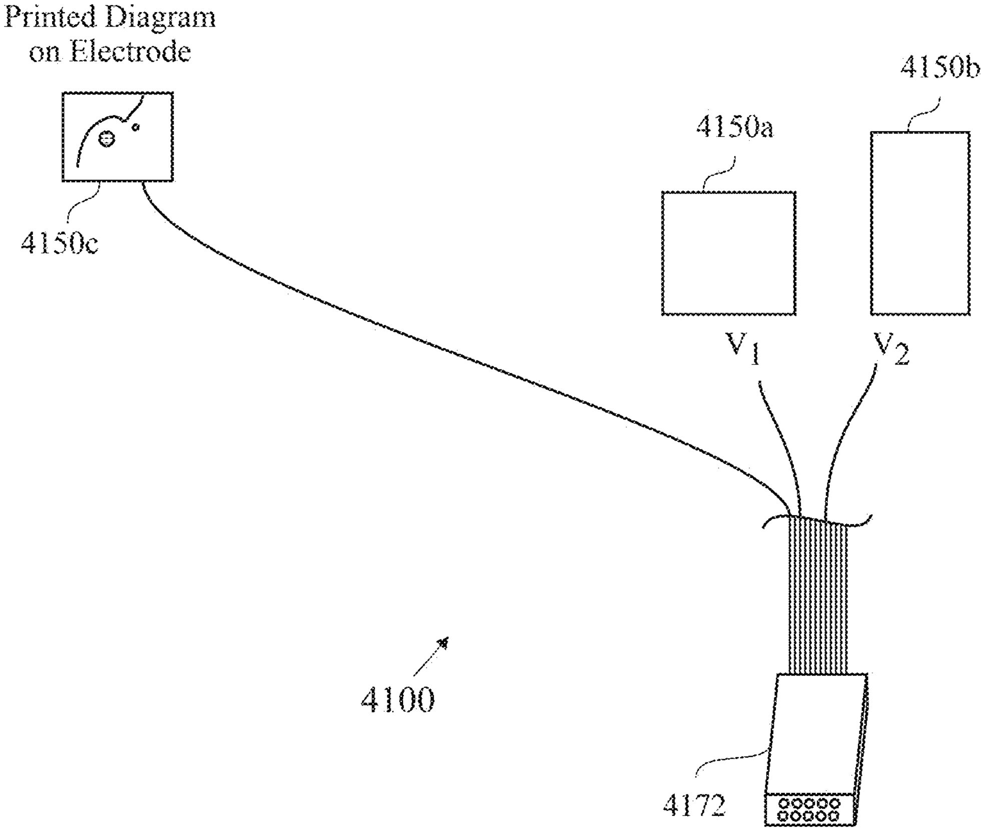
FIG. 41 is an image for an ergonomic cardiac and ECG electrode system.
Figure 42:
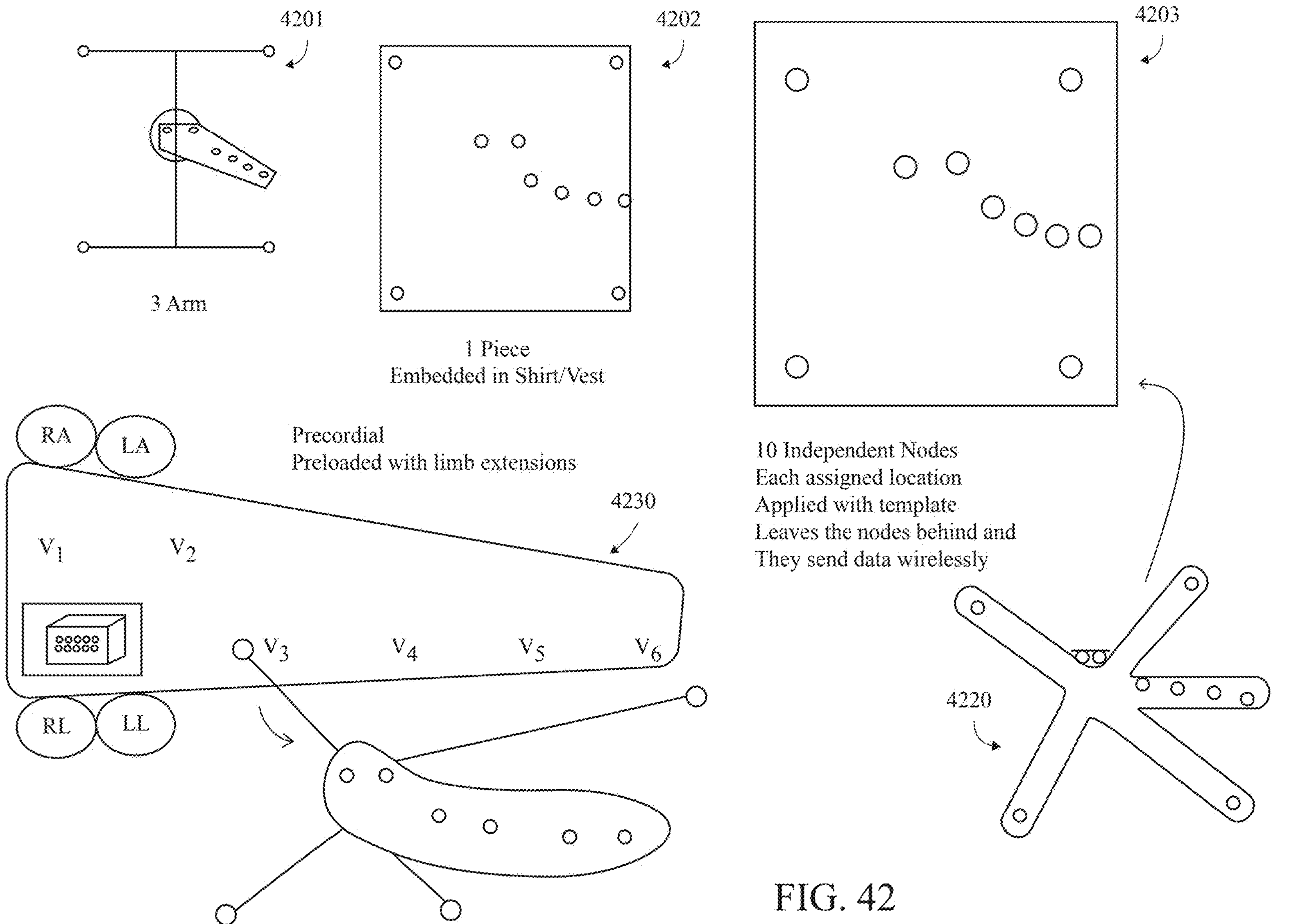
FIG. 42 is an image for an ergonomic cardiac and ECG electrode system.

FIGS. 31 and 31A illustrate an isolated cross-sectional view of a single layer extension. A top surface of the main layer 30 has an integrated printed wire (or elastic electrical conducting material) 60 with a connector 61. Each electrode 50 is attached to an adhesive surface of the main layer 30 with a stud extending through an aperture to connect to the connector 61.

FIGS. 32-42 illustrate various images of an ergonomic cardiac and ECG electrode system with artificial intelligence.

A preferred source for the printed wires is PE874 conductor ink from Intexar Dupont. A conductive elastic rubber material is disclosed in U.S. Pat. No. 8,491,884. A stretchable graphene film material is disclosed in Chen et al., U.S. Patent Publication Number 20150273737. A flexible conductive material comprising silver is disclosed in Taguchi et al., U.S. Patent Publication Number 20130056249.

The emergency cardiac and ECG electrode placement device 20 is capable of being applied to a patient while an emergency vehicle is in motion since the device 20 is applied to and adheres to a patient's chest area, which mitigates signal loss. Likewise, the emergency cardiac and ECG electrode placement device 20 is capable of being applied to a patient that is moving due to a seizure, aggressiveness, and the like.

The entire hospital becomes a telemetry floor since with AI running, the patient can be anywhere in the hospital and thus the patient does not need to be moved to a telemetry floor.

The 12 lead acquisition device allows for monitoring patient in the hospital once the patient is fitted with an EXG device with wireless communication capability.

The AI program constant monitoring of multiple patients wearing the EXG device alerts when a patient is having an event such as a heart attack.

Each EXG device preferably has a wireless transceiver for communicating with a machine running the AI program, which also has a wireless transceiver. The communication protocol is preferably BLUETOOTH, low energy BLUETOOTH, WiFi, and the like.

The AI program preferably runs on an EKG machine.

The electronic medical records ("EMR") data of a patient includes general health records, medical procedure records, allergies, illnesses, and the like of the patient.

The networks utilized with the present invention may be one or more of a wireless network, a wired network or any combination of wireless network and wired network. The networks utilized may include one or more of an Internet network, a wireless local area network ("LAN"), a cellular network, a fiber optics network, a passive optical network, a cable network, a satellite network (e.g., operating in Band C, Band Ku or Band Ka), a Global System for Mobile Communication, a Personal Communication Service, a Personal Area Network Wi-Fi, Fixed Wireless Data, IEEE 802.11a, 802.11b, 802.15.1, 802.11n and 802.11g or any other wired or wireless network for transmitting and receiving a data signal. The network may utilize one or more protocols of one or more network elements to which it is communicatively coupled. The network may translate to or from other protocols to one or more protocols of devices connected to the network. The invention may utilized a plurality of interconnected networks, such as, for example, a service provider network, the Internet, a broadcaster's network, a cable television network, a corporate network, and a home net.

Each of the interface descriptions preferably discloses use of at least one communication protocol to establish handshaking or bi-directional communications. These protocols preferably include but are not limited to XML, HTTP, TCP/IP, Serial, UDP, FTP, Web Services, WAP, SMTP, SMPP, DTS, Stored Procedures, Import/Export, Global Positioning Triangulation, IM, SMS, MMS, GPRS and Flash. The storage of data may be network accessible storage and may be local, remote, or a combination thereof. The storage of data may utilize a redundant array of inexpensive disks, tape, disk, a storage area network, an internet small computer systems interface a common Internet File System, network attached storage, a network file system, or other computer accessible storage. The databases used with the system preferably include but are not limited to MSSQL, Access, MySQL, Progress, Oracle, DB2, Open Source DBs and others. Operating system used with the system preferably include Microsoft 2010, XP, Vista, 2000 Server, 2003 Server, 2008 Server, Windows Mobile, Linux, Android, Unix, I series, AS 400 and Apple OS.

The underlying protocol at a server is preferably Internet Protocol Suite (Transfer Control Protocol/Internet Protocol ("TCP/IP")), and the transmission protocol to receive a file is preferably a file transfer protocol ("FTP"), Hypertext Transfer Protocol ("HTTP"), Secure Hypertext Transfer Protocol ("HTTPS") or other similar protocols. The transmission protocol ranges from SIP to MGCP to FTP and beyond. The protocol at the server is preferably HTTPS.

It is further noted that the software described herein may be tangibly embodied in one or more physical media, such as, but not limited to, a compact disc ("CD"), a digital versatile disc ("DVD"), a floppy disk, a hard drive, read only memory ("ROM"), random access memory ("RAM"), as well as other physical media capable of storing software, or combinations thereof.

Numerous references were made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions. The genomic visualization system may utilize various computing devices including servers, graphical user interfaces, databases, engines, controllers, or other types of computing devices operating individually or collectively. One skilled in the pertinent art will appreciate that the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the invention. In preferred embodiments, the servers, databases, or interfaces preferably exchange data using standardized protocols or algorithms, possibly based on HTTP, HTTPS, AES, public-private key exchanges, web service APIs, known financial transaction protocols, or other electronic information exchanging methods. Data exchanges preferably are conducted over the Internet, LAN, a packet-switched network, WAN, VPN, or other type of packet switched network. One skilled in the pertinent art will appreciate that the form of a computer program product stored by one or more computer-readable storage media having computer-readable program code, or instructions, embodied in or on the storage media. Any suitable computer readable storage media may be utilized, including hard disks, CD-ROMs, optical storage devices, magnetic storage devices, flash devices and/or any combination thereof. In addition, various signals representing data or events as described herein may be transferred between a source and a destination in the form of electromagnetic waves traveling through signal-conducting media such as metal wires, optical fibers, and/or wireless transmission media—e.g. air and/or space. Data may move between various entities in any of the embodiments of the invention via electronic transmission or manual means. Electronic transmission may utilize email, SMS or any other suitable method. Manual exchange may utilize floppy disks, USB drives, CDs, DVDs or any other suitable mechanism.

An exemplary hardware configuration of a computing system utilized with the invention preferably includes at least one processor or central processing unit (CPU). The CPUs are preferably interconnected via a system bus to a RAM, a ROM, input/output (I/O) adapter, user interface adapter, a communication adapter for connecting the system to a data processing network, the Internet, an Intranet, a LAN, or the like, and a display adapter for connecting the bus to a display device.

Any combination of one or more computer readable medium(s) may be utilized with the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium include an electrical connection having one or more wires, a portable computer diskette, a hard disk, a RAM, a ROM, an erasable programmable read-only memory, an optical fiber, a portable CD-ROM, an optical storage device, a magnetic storage device, or any suitable combination of the foregoing. A computer readable storage medium may be any tangible medium that can contain, or store a program for use by or in connection with a system, apparatus, or device running an instruction.

Computer program code for carrying out operations for aspects of the invention may be written in any combination of one or more programming languages, including an object oriented programming language such as Java, Smalltalk, C++ or the like and conventional procedural programming languages, such as the "C" programming language or similar programming languages. The program code may run entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN or the connection may be made to an external computer through the Internet using an Internet Service Provider.

Hypertext Transfer Protocol ("HTTP") is a set of conventions for controlling the transfer of information via the Internet from a web server computer to a client computer, and also from a client computer to a web server, and Hypertext Transfer Protocol Secure ("HTTPS") is a communications protocol for secure communication via a network from a web server computer to a client computer, and also from a client computer to a web server by at a minimum verifying the authenticity of a web site.

Components of a server 1040 of the system 1000, includes a CPU component 1401, a graphics component 1402, PCI/PCI Express 1403, memory 1404, non-removable storage 1407, removable storage 1408, Network Interface 1409, including one or more connections to a fixed network, and SQL database(s) 1045*a*-1045*d*, which includes the venue's CRM. Included in the memory 1404, is an operating system 1405, a SQL server 1406 or other database engine, and computer programs/software 1410. The server 140 also includes at least one computer program configured to receive data uploads and store the data uploads in the SQL database. Alternatively, the SQL server can be installed in a separate server from the venue server 1040.

Wireless Application Protocol ("WAP") is an open, global specification that empowers users with mobile wireless communication devices (such as mobile phones) to easily access data and to interact with Websites over the Internet through such mobile wireless communication device. WAP works with most wireless communication networks such as CDPD, CDMA, GSM, PDC, PHS, TDMA, FLEX, reflex, iDEN, TETRA, DECT, DataTAC, Mobitex and GRPS. WAP can be built on most operating systems including PalmOS, WINDOWS, CE, FLEXOS, OS/9, JavaOS and others.

Web-Server is a computer able to simultaneously manage many Internet information-exchange processes at the same time. Normally, server computers are more powerful than client computers, and are administratively and/or geographically centralized. An interactive-form information-collection process generally is controlled from a server computer, to which the sponsor of the process has access.

SSID (Service Set Identifier) is a 1 to 32 byte string that uniquely names a wireless local area network.

Transfer Control Protocol/Internet Protocol ("TCP/IP") is a protocol for moving files over the Internet.

Internet is the worldwide, decentralized totality of server computers and data-transmission paths which can supply information to a connected and browser-equipped client computer, and can receive and forward information entered from the client computer.

FTP or File Transfer Protocol is a protocol for moving files over the Internet from one computer to another.

BLUETOOTH technology is a standard short range radio link that operates in the unlicensed 2.4 gigaHertz band.

BLUETOOTH LOW ENERGY (aka "BLE" or "BLUETOOTH LE") is a communication format from the Bluetooth Special Interest Group which uses the 2.4 gigaHertz band of BLUETOOTH technology but with a simpler modulation system that supports data pockets ranging from 8 to 27 octets, which are transferred at 1 Mbps.

Application Programming Interface (API) is a collection of computer software code, usually a set of class definitions, that can perform a set of related complex tasks, but has a limited set of controls that may be manipulated by other software-code entities. The set of controls is deliberately limited for the sake of clarity and ease of use, so that programmers do not have to work with the detail contained within the given API itself.

Wireless standards include 802.11a, 802.11b, 802.11g, AX.25, 3G, CDPD, CDMA, GSM, GPRS, radio, microwave, laser, Bluetooth, 802.15, 802.16, and IrDA.

The mobile communication devices utilized with the present invention preferably include mobile phones, smartphones, tablet computers, PDAs and the like. Examples of smartphones include the IPHONE® smartphone from Apple, Inc., BLACKBERRY® smartphones from Research In Motion, the DROID® smartphone from Motorola Mobility Inc., GALAXY S® smartphones from Samsung Electronics Co., Ltd, and many more. Examples of tablet computing devices include the IPAD® tablet from Apple Inc., and the GALAXY TAB® tablet from Samsung Electronics Co., Ltd.

A typical mobile communication device includes an accelerometer 1301, I/O (input/output) 1302, a microphone 1303, a speaker 1304, a GPS chipset 1305, a Bluetooth component 1306, a Wi-Fi component 1307, a 3G/4G component 1308, RAM memory 1309, a main processor 1310, an OS (operating system) 311, applications/software 1312, a Flash memory 1313, SIM card 1314, LCD display 1315, a camera 1316, a power management circuit 1317, a battery 1318 or power source, a magnetometer 1319, and a gyroscope 1320.

Patients with acute coronary syndrome are evaluated with point estimate EKG and serial enzyme testing. Recurrent episodes of chest pain and heart attack are often missed due to delays in EKG acquisition and identification for subtle changes in the EKG. Patients at high risk for disease especially in the era of emergency department overcrowding and delays and triage and patient assessment raise the risk for serious poor outcomes. The authors propose a continuous 12 lead central monitoring algorithm using artificial intelligence to detect subtle changes in the EKG regardless of patient location. With application of a portable EKG monitoring device, the EXG, will interface wirelessly with a central processing unit capable of detecting subtle EKG changes dynamically and alert providers of these changes.

Serial assessments of ST segment and other subtle changes indicative of acute coronary syndrome are time consuming, resource consuming, and can potentially miss changes temporally as these point estimate EKGs are performed.

The ability of AI to perform near continuous evaluation of multiple EKGs on multiple patients simultaneously is something that would be an unconventional and non routine practice scope of any clinician. This novel approach to evaluating patients with presentations concerning for potential acute coronary syndrome will decrease frequency of EKG acquisition but improve patient outcome. This will lead to saving lives, saving time and give clinicians increased confidence in evaluating these patients.

Incorporation of the EXG device coupled with Bluetooth/wifi/RFID technology and a central algorithmic artificial intelligence software system that receives data and that can interpret and identify changes in EKG morphology and other more subtle signs such as R to R wave variability, ventricular vector changes, concerning for acute coronary syndrome in addition to identifying rhythm changes. These subtle changes are often missed by even the most advanced clinicians. This AI will be capable of evaluating simultaneously multiple EKGs on multiple patients across the designated health care system and alert the appropriate clinician of potential changes.

Identifying patients with acute coronary syndrome especially in settings affected by long wait times, triage times, and delays in acquiring repeat EKGs.

Clinicians can miss subtle changes in serial EKGs that AI can more readily identify. Clinicians cannot monitor multiple EKGs on multiple patients effectively and efficiently. Patients typically have timed EKG assessments every several hours and potentially will miss changes when asymptomatic (i.e. without chest pain or other ACS presenting symptoms).

Continuous monitoring with AI will identify more patients with ACS than those without. Decreasing risk of missed acute coronary syndrome and myocardial infarction.

Potential to monitor patients in non patient care setting such as the waiting room, bathroom, home.

The EXG device preferably has Bluetooth connectivity adapter with integrated alarm/alert system. Software and computer system integrated into health care system, cell phone with app, home network, that evaluates EKG data wirelessly transmitted.

EXG device apply to patient chest wall to continuously send EKG signal to central processing AI.

Bluetooth/Wifi/RFID adapter Sends data to central AI system.

AI Processor that evaluates rapid reassessments of EKG wave morphology and rhythm changes to predict and diagnose acute coronary or significant cardiac arrythmias. Tangible software configured with instructions to determine specific changes such as ST segment elevations of more than 1 mm in contiguous leads in comparison to prior EKGs or set norms and alert multiple providers of these changes. The AI will also record these findings and transmit them to providers. The AI will answer the question if there is a change in diagnosis and prognostication to warrant emergent treatment.

Prehospital EKG is obtained on patients for various medical complaints and is used to identify patients with acute coronary syndrome and ST elevation myocardial infarction.

Current model using point estimate EKG interpretation for what is potentially a dynamic and evolving situation. Initial EKG may not be diagnostic and furthermore serial and repeat EKGs are traditionally not a viable option given the limitations inside an ambulance. The ExG system with incorporated bluetooth transmitter and linking to the PACER system enables identification of evolving myocardial infarction and subtle changes consistent with acute coronary syndrome.

Utilizing the EXG device coupled with a bluetooth transmitter and integrated with either a dedicated transmission device with the PACER system or simple smart phone with PACER application. Allows for transmission of data to central AI processor for interpretation of EKG data and observation with rhythm and EKG morphology change detection. Also provides real time information regarding changes in the EKG concerning for acute coronary syndrome to the prehospital provider in the event transmission is not possible. The device will send real time information to advanced care providers enabling faster and more timely detection of acute coronary syndrome. Central processing with physician review of EKG data will also allow for billing for physician services in the prehospital arena that has not traditionally been done.

Dynamic and changing EKG morphology is not currently evaluated with current systems for prehospital providers utilizing point estimate data of only unique and individual EKG data. Current technology does not allow for continuous EKG monitoring for diagnosis of acute coronary syndrome in the prehospital setting.

Application of the EXG device coupled with the PACER system and BLUETOOTH technology enable continuous AI evaluation for acute coronary syndrome during the most critical time of patient evaluation.

One device with one single cable eliminates the need for multiple cumbersome wires attached to patients and limiting movement and portability.

With attached wireless connector allows for even greater patient mobility.

One applied device to replace all associated cables/interfaces for patient complete monitoring while inpatient monitoring is necessary.

The EXG device will have incorporated into it standard transcutaneous oxygen sensors and temperature sensors as well as detect chest wall rise and respiratory rate.

By utilizing the EXG with incorporated multiple sensors one device is applied to the patient throughout the inpatient stay eliminating the need for multiple cables and connections.

One device does it all. Incorporates all relevant non invasive monitoring data into one comprehensive, portable, wireless device.

EXG with pulse ox/temperature/respiratory detector. Transmits relevant data regarding cardiac rhythm, pulse oximetry, respiratory rate and temperature to local and central processing monitors with single cable or wifi/bluetooth adaptor.

Creation of this device will reduce the time to complete an electrocardiogram (ECG) in the pre-hospital and emergency setting, eliminate systematic error in placement and interpretation of an ECG electrode, maintain and place electrodes in the proper anatomic locations across all body types, will not delay management in critical case, maintain proper skin contact through different physiologic responses such as sweat, cold and heat, as well as through medical treatment such as CPR, be easy to train providers in application and placement of ECG electrodes, and be adaptable to scenarios where space and situations limit ECG placement.

One embodiment of the present invention is an emergency cardiac and electrocardiogram (ECG) electrode placement device. The device comprises a body, electrodes, cables, a transcutaneous pulse oximeter positioned on the body, a temperature sensor, and an electrode connector. The body preferably comprises a first extension member, a second extension member, a third extension member, a fourth extension member and a fifth extensions member. The body preferably comprises a base layer composed of a flexible material, an adhesive layer composed of a flexible material, and a backing layer attached to an adhesive surface of the adhesive layer. Each of the electrodes comprises a connection stud, a contact pad interface and a contact pad. The electrode connector is positioned on the body. Each of the second extension member, the third extension member, the fourth extension member and the fifth extension member extends outward from the first extension member. Each cable of the plurality of cables is positioned between the base layer and the adhesive layer, and connected to a corresponding electrode of the plurality of electrodes and connected to the electrode connector. The first extension member comprises a first electrode, a second electrode, a third electrode, a fourth electrode, a fifth electrode and a sixth electrode of the plurality of electrodes. A seventh electrode of the plurality of electrodes is positioned at a far end of the second extension member. An eight electrode of the plurality of electrodes is positioned at a far end of the third extension member. A ninth electrode of the plurality of electrodes is positioned at a far end of the fourth extension member. A tenth electrode of the plurality of electrodes is positioned at a far end of the fifth extension member.

One embodiment of is an EXG with pulse ox/temperature/respiratory detector. It transmits relevant data regarding cardiac rhythm, pulse oximetry, respiratory rate and temperature to local and central processing monitors with single cable or wifi/bluetooth adaptor.

Dunphy et al., U.S. Pat. No. 9,986,929 for an Emergency Cardiac And Electrocardiogram Electrode Placement System, is hereby incorporated by reference in its entirety.

U.S. Provisional Patent Application No. 62/465,752, filed on Mar. 1, 2017, is hereby incorporated by reference in its entirety.

McClung et al., U.S. Pat. No. 10,893,818 for an Emergency Cardiac And Electrocardiogram Electrode Placement System, is hereby incorporated by reference in its entirety.

U.S. Provisional Patent Application No. 62/530,144, filed on Jul. 8, 2017, is hereby incorporated by reference in its entirety.

U.S. Provisional Patent Application No. 62/679,856, filed on Jun. 3, 2018, is hereby incorporated by reference in its entirety.

U.S. Provisional Patent Application No. 62/679,872, filed on Jun. 3, 2018, is hereby incorporated by reference in its entirety.

U.S. Provisional Patent Application No. 62/679,874, filed on Jun. 3, 2018, is hereby incorporated by reference in its entirety.

U.S. Provisional Patent Application No. 62/679,876, filed on Jun. 3, 2018, is hereby incorporated by reference in its entirety.

U.S. Provisional Patent Application No. 62/679,022, filed on Jun. 1, 2018, is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A prehospital artificial intelligence continuous EKG reading and interpretation placement system, the system comprising:
- a device comprising
  - a body composed of a first extension member, a second extension member, a third extension member, a fourth extension member and a fifth extension member, wherein the body comprises a base layer composed of a flexible material, an adhesive layer composed of a flexible material, and
- a backing layer attached to an adhesive surface of the adhesive layer,
  - a plurality of electrodes, each of the plurality of electrodes comprising a connection stud, a contact pad interface and a contact pad,
  - a plurality of cables, and
  - an electrode connector extending from the body;
- a PACER system or a mobile communication device with a PACER mobile application;
- wherein each cable of the plurality of cables is positioned between the base layer and the adhesive layer, and connected to a corresponding electrode of the plurality of electrodes and the electrode connector;
- wherein the first extension member comprises a first electrode, a second electrode, a third electrode, a fourth electrode, a fifth electrode and a sixth electrode of the plurality of electrodes;
- wherein a seventh electrode of the plurality of electrodes is positioned at a far end of the second extension member;
- wherein an eight electrode of the plurality of electrodes is positioned at a far end of the third extension member;
- wherein a ninth electrode of the plurality of electrodes is positioned at a far end of the fourth extension member;
- wherein a tenth electrode of the plurality of electrodes is positioned at a far end of the fifth extension member;
- wherein the device with an incorporated wireless transmitter and linking to the PACER system enables identification of evolving myocardial infarction and subtle changes consistent with acute coronary syndrome.

2. The system according to claim 1 wherein the system allows for transmission of data to a central AI processor for interpretation of EKG data and observation with rhythm and EKG morphology change detection.

3. The system according to claim 1 wherein the system provides real time information regarding changes in the EKG concerning for acute coronary syndrome to the pre-hospital provider in the event transmission is not possible.

4. The system according to claim 1 further comprising a sixth extension member and a seventh extension member, each of the sixth extension member and a seventh extension member having an electrode positioned thereon.

5. The system according to claim 1 further comprising a cable management module.

6. A prehospital artificial intelligence continuous EKG reading and interpretation placement system, the system comprising:

a device comprising a cable management module comprising an upper cover, an upper guide piece, a lower guide piece and a lower cover wherein each of the upper guide piece and the lower guide piece has a plurality of channel therein, a body composed of a first extension member, a second extension member, a third extension member, a fourth extension member and a fifth extension member, wherein the body comprises a base layer composed of a flexible material, an adhesive layer composed of a flexible material, and a backing layer attached to an adhesive surface of the adhesive layer, a plurality of electrodes, each of the plurality of electrodes comprising a connection stud, a contact pad interface and a contact pad, a plurality of cables, and an electrode connector;

a PACER system or a mobile communication device with a PACER mobile application;

wherein each of the second extension member, the third extension member, the fourth extension member and the fifth extension member extends outward from the cable management module;

wherein each cable of the plurality of cables is positioned between the base layer and the adhesive layer, routed through a channel of the plurality of channels, and connected to a corresponding electrode of the plurality of electrodes and the electrode connector;

wherein the device with an incorporated wireless transmitter and linking to the PACER system enables identification of evolving myocardial infarction and subtle changes consistent with acute coronary syndrome.

7. The system according to claim 6 wherein the first extension member comprises a first electrode, a second electrode, a third electrode, a fourth electrode, a fifth electrode and a sixth electrode of the plurality of electrodes; wherein a seventh electrode of the plurality of electrodes is positioned at a far end of the second extension member; wherein an eight electrode of the plurality of electrodes is positioned at a far end of the third extension member; wherein a ninth electrode of the plurality of electrodes is positioned at a far end of the fourth extension member; and wherein a tenth electrode of the plurality of electrodes is positioned at a far end of the fifth extension member.

8. The system according to claim 6 wherein each extension member has a width ranging from 1 cm to 10 cm, and a length ranging from 5 cm to 20 cm.

9. The system according to claim 6 further comprising a plurality of external electrodes.

10. The system according to claim 6 further comprising a sixth extension member and a seventh extension member, each of the sixth extension member and a seventh extension member having an electrode positioned thereon.

11. A prehospital artificial intelligence continuous EKG reading and interpretation placement system, the system comprising:

a device comprising a body composed of a plurality of extension members, wherein the body comprises a main layer composed of a flexible material, the main layer having a top surface an adhesive surface, and a backing layer attached to an adhesive surface of the adhesive layer, a plurality of electrodes, each of the plurality of electrodes positioned on the adhesive surface of the main layer, a plurality of printed wires, and an electrode connector cable extending from the body;

a PACER system or a mobile communication device with a PACER mobile application;

wherein each printed wire of the plurality of printed wires is printed on the top surface of the main layer, and connected to a corresponding electrode of the plurality of electrodes and the electrode connector cable;

wherein the device with an incorporated wireless transmitter and linking to the PACER system enables identification of evolving myocardial infarction and subtle changes consistent with acute coronary syndrome.

12. The system according to claim 11 wherein each extension member has a width ranging from 1 cm to 10 cm, and a length ranging from 5 cm to 20 cm.

13. The system according to claim 11 wherein each of the plurality of electrodes is composed of an AgCl gel electrode plate.

14. The system according to claim 11 wherein the plurality of extension members comprises a center extension member, first extension member, a second extension member, a third extension member, and a fourth extension member.

15. The system according to claim 11 wherein the printed wire is composed of a conducting ink or printed electrically conductive material.

16. The system according to claim 11 wherein the electrical conducting elastic material is graphene yarn, silver/silver-chloride wire, or a conductive rubber.

* * * * *